(12) United States Patent
Wang et al.

(10) Patent No.: US 10,065,973 B2
(45) Date of Patent: Sep. 4, 2018

(54) SUBSTITUTED AMINOTHIAZOLOPYRIMIDINEDIONE FOR THE TREATMENT AND PROPHYLAXIS OF VIRUS INFECTION

(71) Applicant: Hoffmann-La Roche Inc., Little Falls, NJ (US)

(72) Inventors: Baoxia Wang, Shanghai (CN); Lisha Wang, Riehen (CH); Hongying Yun, Shanghai (CN); Xiufang Zheng, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/809,109

(22) Filed: Nov. 10, 2017

(65) Prior Publication Data

US 2018/0093999 A1    Apr. 5, 2018

Related U.S. Application Data

(63) Continuation of application No. PCT/EP2016/060251, filed on May 9, 2016.

(51) Int. Cl.
*C07D 513/04*    (2006.01)
*A61P 31/20*    (2006.01)

(52) U.S. Cl.
CPC ............ *C07D 513/04* (2013.01); *A61P 31/20* (2018.01)

(58) Field of Classification Search
CPC ............................... C07D 513/04; A61P 31/20
USPC ..................................................... 514/260.1
See application file for complete search history.

(56) References Cited

U.S. PATENT DOCUMENTS

| | | | |
|---|---|---|---|
| 5,476,659 A | 12/1995 | Goodman et al. | |
| 6,121,431 A * | 9/2000 | Classon | A61K 31/505 536/26.23 |
| 7,560,544 B2 | 7/2009 | Webber et al. | |
| 7,709,448 B2 | 4/2010 | Haley et al. | |
| 9,441,008 B2 * | 9/2016 | Chen | C07D 513/04 |
| 9,676,793 B2 * | 6/2017 | Schwitter | C07D 513/04 |
| 2005/0004144 A1 | 6/2005 | Carson et al. | |
| 2016/0176899 A1 * | 6/2016 | Schwitter | C07D 513/04 514/260.1 |
| 2016/0194350 A1 * | 7/2016 | Chen | C07D 513/04 514/43 |
| 2016/0326209 A1 * | 11/2016 | Chen | C07H 19/24 19/24 |
| 2018/0000824 A1 * | 1/2018 | Dai | A61K 31/519 |

FOREIGN PATENT DOCUMENTS

| | | | |
|---|---|---|---|
| EP | 0 343 945 A2 | 11/1989 | |
| EP | 1 072 607 A2 | 1/2001 | |
| WO | 89/05649 A1 | 6/1989 | |
| WO | 98/16184 A2 | 4/1998 | |
| WO | 2005/016235 A2 | 2/2005 | |
| WO | 2005/025583 A2 | 3/2005 | |
| WO | 2006/066080 A1 | 6/2006 | |
| WO | 2007/135134 A1 | 11/2007 | |
| WO | 2007/150002 A2 | 12/2007 | |
| WO | 2008/011406 A2 | 1/2008 | |
| WO | 2008/140549 A1 | 11/2008 | |
| WO | 2009/026292 A1 | 2/2009 | |
| WO | 2016/091698 A1 | 6/2016 | |
| WO | WO2016146598 | * | 9/2016 |
| WO | WO2017001307 | * | 1/2017 |

OTHER PUBLICATIONS

Tseng; J. Med. Chem., 1991, 34, 343-349. (Year: 1991).*
Ioannidis; Nucleosides and Nucleotides 1992, 116, 1205-1218. (Year: 1992).*
Fletcher; Current Opinion in Investigational Drugs 2006, 7, 702-708. (Year: 2006).*
Xiang; Nucleosides, Nucleotides, and Nucleic Acids, 2007, 26, 635-640. (Year: 2007).*
Asselah et al., "Interferon therapy for chronic hepatitis B" Clin Liver Dis 11:839-849 ( 2007).
Connolly et al., "New developments in Tool-like receptor targeted therapeutics" Current Opinion in Pharmacology 12:510-518 ( 2012).
Gane et al., "Safety and pharmacodynamics of oral TLR-7 agonist GS-9620 in patients with chronic hepatitis B" Abstract Ann. Meeting Am. Assoc. Study Liver Dis, Washington, D.C., pp. 661A, Abstract 946 ( Nov. 2013).
Hemmi et al., "Small anti-viral compounds activate immune cells via the TLR7 MyD88-dependent signaling pathway" Nature Immunology 3(2):196 ( 2002).
ISR of PCT/EP2016/060251 (dated Jul. 18, 2016).
Kaisho et al., "Turning NF-kB and IRFs on and off in DC" Trends in Immunology 29(7):329-336 ( 2008).
Roethle et al., "Identification and Optimization of Pteridinone Toll-like Receptor 7 (TLR7) Agonists for the Oral Treatment of Viral Hepatitis" Journal of Medicinal Chemistry 56(18):7324-7333 (Sep. 26, 2013).

* cited by examiner

Primary Examiner — Daniel R Carcanague
(74) Attorney, Agent, or Firm — Jonathan Duffield

(57) ABSTRACT

The present invention relates to compounds of formula (I),

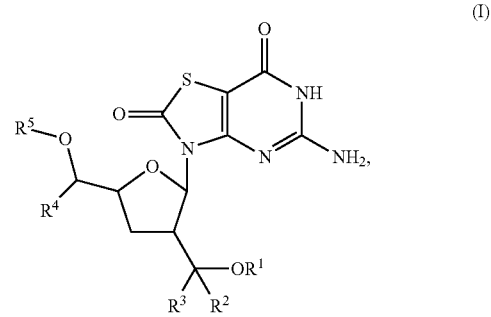

wherein $R^1$ to $R^5$ are as described herein, and their prodrugs or pharmaceutically acceptable salt, enantiomer or diastereomer thereof, and compositions including the compounds and methods of using the compounds.

31 Claims, No Drawings

SUBSTITUTED AMINOTHIAZOLOPYRIMIDINEDIONE FOR THE TREATMENT AND PROPHYLAXIS OF VIRUS INFECTION

RELATED APPLICATIONS

This application is a continuation of International Application No. PCT/EP2016/060251, filed May 9, 2016, claiming priority to International Application No. PCT/CN2015/078752 filed May 12, 2015, each of which are incorporated herein by reference in its entirety.

The present invention relates to novel substituted aminothiazolopyrimidinedione and their corresponding derivatives that have Toll-like receptor agonism activity and their prodrugs thereof, as well as their manufacture, pharmaceutical compositions containing them and their potential use as medicaments.

FIELD OF THE INVENTION

The present invention relates to compounds of formula (I) and (Ia),

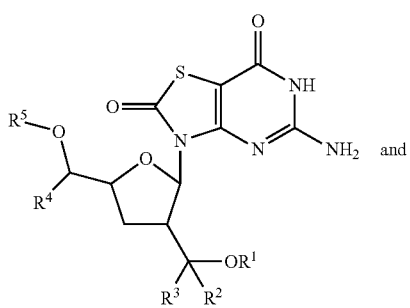

(I)

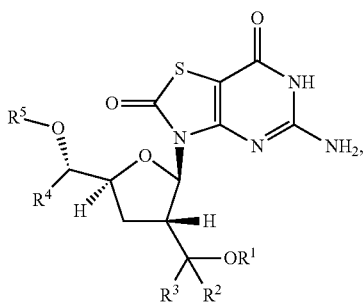

(Ia)

and their prodrugs, compounds of formula (II) and (IIa),

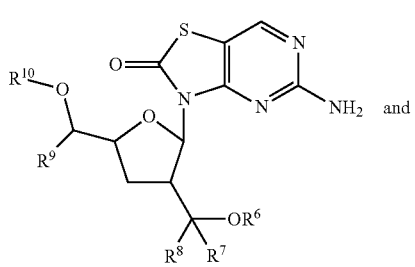

(II)

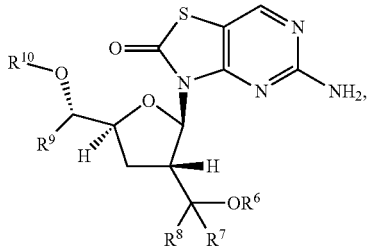

(IIa)

wherein $R^1$ to $R^{10}$ are described below, or pharmaceutically acceptable salt, enantiomer or diastereomer thereof.

Toll-like receptors (TLRs) detect a wide range of conserved pathogen-associated molecular patterns (PAMPs). They play an important role of sensing invading pathogens and subsequent initiation of innate immune responses. There are 10 known members of the TLR family in human, which are type I transmembrane proteins featuring an extracellular leucine-rich domain and a cytoplasmic tail that contains a conserved Toll/interleukin (IL)-1 receptor (TIR) domain. Within this family, TLR3, TLR7 TLR8, and TLR9 are located within endosomes. TLR7 can be activated by binding to a specific small molecule ligand (i.e., TLR7 agonist) or its native ligand (i.e., single-stranded RNA, ssRNA). Following binding of ssRNA to TLR7, the receptor in its dimerized form is believed to undergo a structural change leading to the subsequent recruitment of adapter proteins at its cytoplasmic domain, including the myeloid differentiation primary response gene 88 (MyD88). Following the initiation of the receptor signalling cascade via the MyD88 pathway, cytoplasmic transcription factors such as interferon regulatory factor 7 (IRF-7) and nuclear factor kappa B (NF-κB) are activated. These transcription factors then translocate to the nucleus and initiate the transcription of various genes, e.g., IFN-α and other antiviral cytokine genes. TLR7 is predominately expressed on plasmacytoid cells, and also on B-cells. Altered responsiveness of immune cells might contribute to the reduced innate immune responses during chronic viral infections. Agonist-induced activation of TLR7 might therefore represent a novel approach for the treatment of chronic viral infections. (D. J Connolly and L. A J O'Neill, Current Opinion in Pharmacology 2012, 12:510-518, P. A. Roethle et al, J. Med. Chem. 2013, 56, 7324-7333).

The current therapy of chronic HBV infection is based on two different types of drugs: the traditional antiviral nucleos(t)ide analogues and the more recent Pegylated IFN-α (PEG-IFN-α). The oral nucleos(t)ide analogues act by suppressing the HBV replication. This is a life-long course of treatment during which drug resistance often occurs. As an alternative option, Pegylated IFN-α (PEG-IFN-α) has been used to treat some chronic infected HBV patients within finite therapy duration. Although it has achieved seroconversion in HBeAg at least in a small percentage of HBV patients, the adverse effect makes it poorly tolerable. Notably, functional cure defined as HBsAg seroconversion is very rare with both current therapies. A new generation therapeutic option to treat HBV patients for a functional cure is therefore of urgent need. Treatment with an oral TLR7 agonist represents a promising solution to provide greater efficacy with better tolerability. Pegylated IFN-α (PEG-IFN-α) is currently used to treat chronic HBV and is an alternative to potentially life-long treatment with antiviral nucleos(t)ide analogues. In a subset of chronic HBV patients, PEG-IFN-α therapy can induce sustained immunologic control of the virus following a finite duration of therapy. However, the percentage of HBV patients that achieve seroconversion with interferon therapy is low (up to 27% for HBeAg-positive patients) and the treatment is typically poorly tolerated. Furthermore, functional cure (defined as HBsAg loss and seroconversion) is also very infrequent with both PEG-IFN-α and nucleos(t)ide treatment. Given these limitations, there is an urgent need for improved therapeutic options to treat and induce a functional cure for chronic HBV. Treatment with an oral, small-molecule TLR7 agonist is a promising approach that has the potential to provide greater efficacy and tolerability (T. Asselah et al, Clin Liver Dis 2007, 11, 839-849).

In fact, several identified TLR7 agonists have been considered for therapeutic purposes. So far Imiquimod (ALDARA™) is a U.S. FDA approved TLR7 agonist drug for topical use to treat skin lesions by human papillomavirus. The TLR7/8 dual agonist resiquimod (R-848) and the TLR7 agonist 852A have been evaluated for treating human genital herpes and chemotherapy-refractory metastatic melanoma, respectively. ANA773 is an oral pro-drug TLR7 agonist, developed for the treatment of patients with chronic hepatitis C virus (HCV) infection and chronic hepatitis B infection. GS-9620 is an orally available TLR7 agonist. A phase Ib study demonstrated that treatment with GS-9620 was safe, well tolerated and resulted in dose-dependent ISG15 mRNA induction in patients with chronic hepatitis B (E. J. Gane et al, Annu Meet Am Assoc Study Liver Dis (November 1-5, Washington, D.C.) 2013, Abst 946). Therefore there is high unmet clinical need for developing potent and safe TLR7 agonists as new HBV treatment to offer more therapeutic solutions or replace existing partly effective treatment.

SUMMARY OF THE INVENTION

The present invention provides a series of novel 3-substituted 5-amino-6H-thiazolo[4,5-d]pyrimidine-2,7-dione compounds, that have Toll-like receptor agonism activity and their prodrugs. The invention also provides the bioactivity of such compounds to induce SEAP level increase by activating Toll-like receptors, such as TLR7 receptor, the metabolic conversion of prodrugs to parent compounds in the presence of human hepatocytes, and the therapeutic or prophylactic use of such compounds and their pharmaceutical compositions comprising these compounds and their prodrugs to treat or prevent infectious disease like HBV or HCV. The present invention also provides compounds with superior activity.

The present invention relates to novel compounds of formula (I) and (Ia),

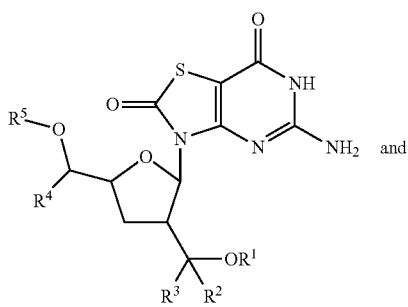

(I)

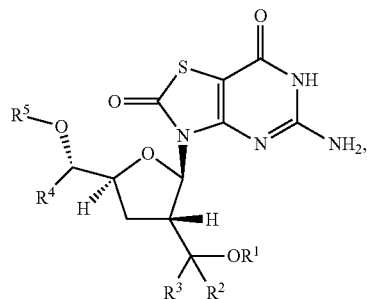

(Ia)

wherein
$R^1$ is H, $C_{1-6}$alkyl, $C_{2-6}$alkenyl, phenyl$C_{1-6}$alkyl, $C_{1-6}$alkylcarbonyl, $C_{1-6}$alkoxycarbonyl, phenylcarbonyl;
$R^2$ and $R^3$ are independently selected from H, $C_{1-6}$alkyl, $C_{3-7}$cycloalkyl, phenyl and pyridinyl, said phenyl and pyridinyl being unsubstituted or substituted with one to three substituents independently selected from $C_{1-6}$alkyl, halogen and $C_{1-6}$alkoxy;
$R^4$ is H or $C_{1-6}$alkyl;
$R^5$ is H or $C_{1-6}$alkylcarbonyl;
or pharmaceutically acceptable salt, enantiomer or diastereomer thereof.

The present invention also relates to the prodrugs of formula (II) and (IIa),

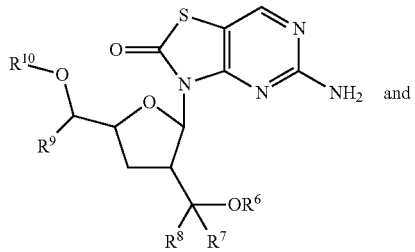

(II)

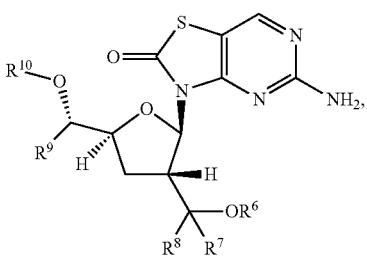

(IIa)

wherein
$R^6$ is H, $C_{1-6}$alkyl, $C_{2-6}$alkenyl, phenyl$C_{1-6}$alkyl, $C_{1-6}$alkylcarbonyl, $C_{1-6}$alkoxycarbonyl, phenylcarbonyl;
$R^7$ and $R^8$ are independently selected from H, $C_{1-6}$alkyl, $C_{3-7}$cycloalkyl, phenyl and pyridinyl, said phenyl and pyridinyl being unsubstituted or substituted with one to three substituents independently selected from $C_{1-6}$alkyl, halogen and $C_{1-6}$alkoxy;
$R^9$ is H or $C_{1-6}$alkyl;
$R^{10}$ is H or $C_{1-6}$alkylcarbonyl;
or pharmaceutically acceptable salt, enantiomer or diastereomer thereof.

The invention also relates to their manufacture, medicaments based on a compound in accordance with the invention and their production as well as the use of compounds of formula (I) or (Ia) or their prodrugs, formula (II) or (IIa), thereof as TLR7 agonist. Accordingly, the compounds of formula (I) and (Ia) or their prodrugs of formula (II) and (IIa) are useful for the treatment or prophylaxis of HBV and/or HCV infection with Toll-like receptors agonism.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

Definitions

As used herein, the term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, iso-butyl, tert-butyl and the like. Particular "$C_{1-6}$alkyl" groups are methyl, ethyl and n-propyl.

The term "$C_{2-6}$alkenyl" denotes an unsaturated, linear or branched chain alkenyl group containing 2 to 6, particularly 2 to 4 carbon atoms, for example vinyl, propenyl, allyl, butenyl and the like. Particular "$C_{2-6}$alkenyl" group is allyl and vinyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl.

The term "$C_{1-6}$alkoxy" refers to a group $C_{1-6}$alkyl-O—, wherein the "$C_{1-6}$alkyl" is as defined above. Particular "$C_{1-6}$alkoxy" group is methoxy or ethoxy.

The term "carbonyl" alone or in combination refers to the group —C(O)—.

The term "$C_{1-6}$alkylcarbonyl" refers to a group $C_{1-6}$alkyl-C(O)—, wherein the "$C_{1-6}$alkyl" is as defined above. Particular "$C_{1-6}$alkylcarbonyl" group is acetyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) or (Ia) and their prodrugs which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The compounds of the invention may exhibit the phenomenon of tautomerism. While the formula drawings cannot expressly depict all possible tautomeric forms, it is to be understood they are intended to represent any tautomeric form of the depicted compound and are not to be limited merely to a specific compound form depicted by the formula drawings. For example, it is understood for formula (III) that regardless of whether or not the substituents are shown in their enol or their keto form, they represent the same compound (as shown in the example below).

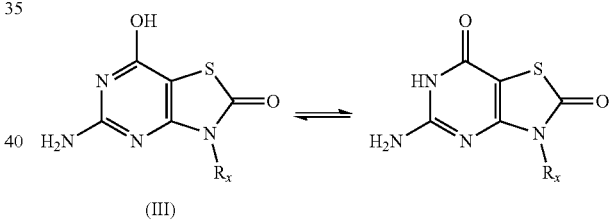

(III)

$R_x$ refers to any feasible substituent.

Some of the compounds of the present invention may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form. As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.). Additionally, compounds of formula (I) and (Ia) and their prodrugs, formula (II) and (IIa), and other compounds of the invention are intended to cover solvated as well as unsolvated forms of the identified structures. For example, formula (I) or (Ia) includes compounds of the indicated structure in both hydrated and non-hydrated forms. Other examples of solvates include the structures in combination with isopropanol, ethanol, methanol, DMSO, ethyl acetate, acetic acid, or ethanolamine.

The term "prodrug" denotes a form or derivative of a compound which is metabolized in vivo, e.g., by biological fluids or enzymes by a subject after administration, into a pharmacologically active form of the compound in order to produce the desired pharmacological effect. Prodrugs are described e.g. in "The Organic Chemistry of Drug Design and Drug Action", by Richard B. Silverman, Academic Press, San Diego, 2004, Chapter 8 Prodrugs and Drug Delivery Systems, pp. 497-558.

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

TLR7 Agonist and Prodrug

The present invention relates to a compound of formula (I),

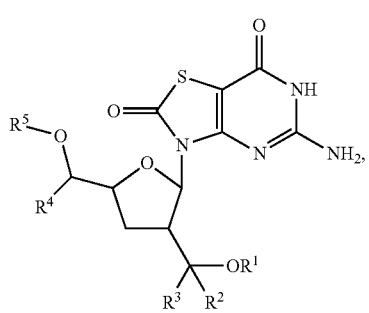

wherein
$R^1$ is H, $C_{1-6}$alkyl, $C_{2-6}$alkenyl, phenyl$C_{1-6}$alkyl, $C_{1-6}$alkylcarbonyl, $C_{1-6}$alkoxycarbonyl, phenylcarbonyl;

$R^2$ and $R^3$ are independently selected from H, $C_{1-6}$alkyl, $C_{3-7}$cycloalkyl, phenyl and pyridinyl, said phenyl and pyridinyl being unsubstituted or substituted with one to three substituents independently selected from $C_{1-6}$alkyl, halogen and $C_{1-6}$alkoxy;

$R^4$ is H or $C_{1-6}$alkyl;

$R^5$ is H or $C_{1-6}$alkylcarbonyl;

or pharmaceutically acceptable salt, enantiomer or diastereomer thereof.

Another embodiment of present invention is (ii) a compound of formula (Ia),

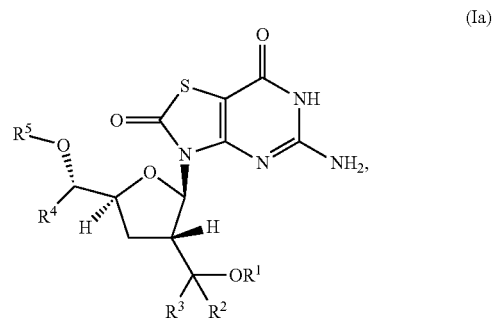

wherein
$R^1$ is H, $C_{1-6}$alkyl, $C_{2-6}$alkenyl, phenyl$C_{1-6}$alkyl, $C_{1-6}$alkylcarbonyl, $C_{1-6}$alkoxycarbonyl, phenylcarbonyl;

$R^2$ and $R^3$ are independently selected from H, $C_{1-6}$alkyl, $C_{3-7}$cycloalkyl, phenyl and pyridinyl, said phenyl and pyridinyl being unsubstituted or substituted with one to three substituents independently selected from $C_{1-6}$alkyl, halogen and $C_{1-6}$alkoxy;

$R^4$ is H or $C_{1-6}$alkyl;

$R^5$ is H or $C_{1-6}$alkylcarbonyl;

or pharmaceutically acceptable salt, enantiomer or diastereomer thereof.

A further embodiment of present invention is (iii) a compound of formula (I) or (Ia), wherein $R^1$ is H, $C_{1-6}$alkyl, $C_{1-6}$alkylcarbonyl, $C_{1-6}$alkoxycarbonyl or phenylcarbonyl; or pharmaceutically acceptable salt, enantiomer or diastereomer thereof.

A further embodiment of present invention is (iv) a compound of formula (I) or (Ia), wherein $R^1$ is H, methyl, acetyl, ethoxycarbonyl or phenylcarbonyl; or pharmaceutically acceptable salt, enantiomer or diastereomer thereof.

A further embodiment of present invention is (v) a compound of formula (I) or (Ia), wherein $R^2$ and $R^3$ are independently selected from H, $C_{1-6}$alkyl and phenyl, said phenyl being unsubstituted or substituted with one to three substituents independently selected from $C_{1-6}$alkyl, halogen and $C_{1-6}$alkoxy; provided that $R^2$ and $R^3$ are not H simultaneously; or pharmaceutically acceptable salt, enantiomer or diastereomer thereof.

A further embodiment of present invention is (vi) a compound of formula (I) or (Ia), wherein $R^2$ and $R^3$ are independently selected from H, methyl, ethyl, phenyl, chlorophenyl and methoxyphenyl; provided that $R^2$ and $R^3$ are not H simultaneously; or pharmaceutically acceptable salt, enantiomer or diastereomer thereof.

A further embodiment of present invention is (vii) a compound of formula (I) or (Ia), wherein R¹ is H;

R² and R³ are independently selected from H, $C_{1-6}$alkyl and phenyl, provided that R² and R³ are not H simultaneously;

R⁴ is H or $C_{1-6}$alkyl;

R⁵ is H or $C_{1-6}$alkylcarbonyl;

or pharmaceutically acceptable salt, enantiomer or diastereomer thereof.

A further embodiment of present invention is (viii) a compound of formula (I) or (Ia), wherein R¹ is H;

R² and R³ are independently selected from H, methyl and phenyl, provided that R² and R³ are not H simultaneously;

R⁴ is H or ethyl;

R⁵ is H or acetyl;

or pharmaceutically acceptable salt, enantiomer or diastereomer thereof.

Another embodiment of present invention is that (ix) particular compounds of formula (I) or (Ia) are the following:

5-Amino-3-[(2R,3S,5S)-3-(1-hydroxyethyl)-5-(hydroxymethyl)tetrahydrofuran-2-yl]-6H -thiazolo[4,5-d]pyrimidine-2,7-dione;

5-Amino-3-[(2R,3S,5S)-3-[cyclopropyl(hydroxy)methyl]-5-(hydroxymethyl)tetrahydrofuran-2-yl]-6H-thiazolo[4,5-d]pyrimidine-2,7-dione;

5-Amino-3-[(2R,3S,5S)-5-(hydroxymethyl)-3-(1-hydroxypropyl)tetrahydrofuran-2-yl]-6H -thiazolo[4,5-d]pyrimidine-2,7-dione;

5-Amino-3-[(2R,3S,5S)-5-(hydroxymethyl)-3-[hydroxy(phenyl)methyl]tetrahydrofuran-2-yl]-6H-thiazolo[4,5-d]pyrimidine-2,7-dione;

5-Amino-3-[(2R,3S,5S)-3-[hydroxy-(2-methoxyphenyl)methyl]-5-(hydroxymethyl)tetrahydrofuran-2-yl]-6H-thiazolo[4,5-d]pyrimidine-2,7-dione;

5-Amino-3-[(2R,3S,5S)-3-[(2-chlorophenyl)-hydroxymethyl]-5-(hydroxymethyl)tetrahydrofuran-2-yl]-6H-thiazolo[4,5-d]pyrimidine-2,7-dione;

5-Amino-3-[(2R,3S,5S)-5-(hydroxymethyl)-3-[(S)-hydroxy(2-pyridyl)methyl]tetrahydrofuran-2-yl]-6H-thiazolo[4,5-d]pyrimidine-2,7-dione;

5-Amino-3-[(2R,3S,5S)-5-(hydroxymethyl)-3-(1-hydroxy-1-methyl-ethyl)tetrahydrofuran-2-yl]-6H-thiazolo[4,5-d]pyrimidine-2,7-dione;

[(1R)-1-[(2R,3S,5S)-2-(5-Amino-2,7-dioxo-6H-thiazazo[4,5-d]pyrimidin-3-yl)-5-[(1S)-1-hydroxypropyl]tetrahydrofuran-3-yl]ethyl] acetate;

[(1S)-1-[(2R,3S,5S)-2-(5-amino-2,7-dioxo-6H-thiazolo[4,5-d]pyrimidin-3-yl)-5-[(1S)-1-hydroxypropyl]tetrahydrofuran-3-yl]ethyl] acetate;

5-Amino-3-[(2R,3S,5S)-3-[(1R)-1-hydroxyethyl]-5-[(1S)-1-hydroxypropyl]tetrahydrofuran-2-yl]-6H-thiazolo[4,5-d]pyrimidine-2,7-dione;

5-Amino-3-[(2R,3S,5S)-3-[(1S)-1-hydroxyethyl]-5-[(1S)-1-hydroxypropyl]tetrahydrofuran-2-yl]-6H-thiazolo[4,5-d]pyrimidine-2,7-dione;

[(1R)-1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]ethyl] ethyl carbonate;

[(1R)-1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]ethyl] benzoate;

5-Amino-3-[(2R,3S,5S)-5-[(1S)-1-hydroxypropyl]-3-[(1R)-1-methoxyethyl]tetrahydrofuran-2-yl]-6H-thiazolo[4,5-d]pyrimidine-2,7-dione;

5-Amino-3-[(2R,3S,5S)-3-[(1R)-1-benzyloxyethyl]-5-[(1S)-1-hydroxypropyl]tetrahydrofuran-2-yl]-6H-thiazolo[4,5-d]pyrimidine-2,7-dione;

3-[(2R,3S,5S)-3-[(1R)-1-Allyloxyethyl]-5-[(1S)-1-hydroxypropyl]tetrahydrofuran-2-yl]-5-amino-6H-thiazolo[4,5-d]pyrimidine-2,7-dione;

5-Amino-3-[(2R,3S,5S)-5-[(1S)-1-hydroxypropyl]-3-[(1S)-1-methoxyethyl]tetrahydrofuran-2-yl]-6H-thiazolo[4,5-d]pyrimidine-2,7-dione;

[(1S)-1-[(2S,4S,5R)-5-(5-Amino-2,7-dioxo-6H-thiazolo[4,5-d]pyrimidin-3-yl)-4-[(1R)-1-hydroxyethyl]tetrahydrofuran-2-yl]propyl] acetate;

5-Amino-3-[(2R,3S,5S)-3-[hydroxy(phenyl)methyl]-5-[(1S)-1-hydroxypropyl]tetrahydrofuran-2-yl]-6H-thiazolo[4,5-d]pyrimidine-2,7-dione;

[1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]-1-methyl-ethyl] acetate;

5-Amino-3-[(2R,3S,5S)-3-(1-hydroxy-1-methyl-ethyl)-5-[(1S)-1-hydroxypropyl]tetrahydrofuran-2-yl]-6H-thiazolo[4,5-d]pyrimidine-2,7-dione;

or pharmaceutically acceptable salt, enantiomer or diastereomer thereof.

Another embodiment of present invention is that (x) more particular compounds of formula (I) or (Ia) are the following:

5-Amino-3-[(2R,3S,5S)-3-(1-hydroxyethyl)-5-(hydroxymethyl)tetrahydrofuran-2-yl]-6H-thiazolo[4,5-d]pyrimidine-2,7-dione;

5-Amino-3-[(2R,3S,5S)-5-(hydroxymethyl)-3-(1-hydroxy-1-methyl-ethyl)tetrahydrofuran-2-yl]-6H-thiazolo[4,5-d]pyrimidine-2,7-dione;

5-Amino-3-[(2R,3S,5S)-3-[(1R)-1-hydroxyethyl]-5-[(1S)-1-hydroxypropyl]tetrahydrofuran-2-yl]-6H-thiazolo[4,5-d]pyrimidine-2,7-dione;

[(1S)-1-[(2S,4S,5R)-5-(5-Amino-2,7-dioxo-6H-thiazolo[4,5-d]pyrimidin-3-yl)-4-[(1R)-1-hydroxyethyl]tetrahydrofuran-2-yl]propyl] acetate;

5-Amino-3-[(2R,3S,5S)-3-[hydroxy(phenyl)methyl]-5-[(1S)-1-hydroxypropyl]tetrahydrofuran-2-yl]-6H-thiazolo[4,5-d]pyrimidine-2,7-dione;

5-Amino-3-[(2R,3S,5S)-3-(1-hydroxy-1-methyl-ethyl)-5-[(1S)-1-hydroxypropyl]tetrahydrofuran-2-yl]-6H-thiazolo[4,5-d]pyrimidine-2,7-dione;

or pharmaceutically acceptable salt, enantiomer or diastereomer thereof.

Another embodiment of present invention is (xi) a compound of formula (II),

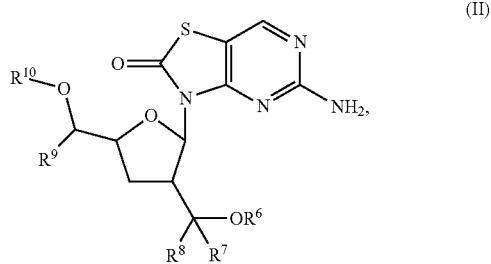

wherein

R⁶ is H, $C_{1-6}$alkyl, $C_{2-6}$alkenyl, phenyl$C_{1-6}$alkyl, $C_{1-6}$alkylcarbonyl, $C_{1-6}$alkoxycarbonyl, phenylcarbonyl;

R⁷ and R⁸ are independently selected from H, $C_{1-6}$alkyl, $C_{3-7}$cycloalkyl, phenyl and pyridinyl, said phenyl and pyridinyl being unsubstituted or substituted with one to three substituents independently selected from $C_{1-6}$alkyl, halogen and $C_{1-6}$alkoxy;

$R^9$ is H or $C_{1-6}$alkyl;
$R^{10}$ is H or $C_{1-6}$alkylcarbonyl;
or pharmaceutically acceptable salt, enantiomer or diastereomer thereof.

Another embodiment of present invention is (xii) a compound of formula (IIa),

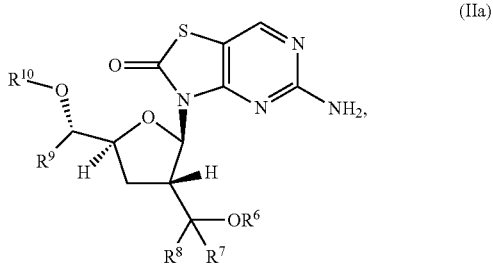

(IIa)

wherein
$R^6$ is H, $C_{1-6}$alkyl, $C_{2-6}$alkenyl, phenyl$C_{1-6}$alkyl, $C_{1-6}$alkylcarbonyl, $C_{1-6}$alkoxycarbonyl, phenylcarbonyl;
$R^7$ and $R^8$ are independently selected from H, $C_{1-6}$alkyl, $C_{3-7}$cycloalkyl, phenyl and pyridinyl, said phenyl and pyridinyl being unsubstituted or substituted with one to three substituents independently selected from $C_{1-6}$alkyl, halogen and $C_{1-6}$alkoxy;
$R^9$ is H or $C_{1-6}$alkyl;
$R^{10}$ is H or $C_{1-6}$alkylcarbonyl;
or pharmaceutically acceptable salt, enantiomer or diastereomer thereof.

A further embodiment of present invention is (xiii) a compound of formula (II) or (IIa), wherein $R^6$ is H, $C_{1-6}$alkyl, $C_{1-6}$alkylcarbonyl, $C_{1-6}$alkoxycarbonyl or phenylcarbonyl; or pharmaceutically acceptable salt, enantiomer or diastereomer thereof.

A further embodiment of present invention is (xiv) a compound of formula (II) or (IIa), wherein $R^6$ is H, methyl, acetyl, isopropylcarbonyl, tert-butylcarbonyl, isobutylcarbonyl, ethoxycarbonyl or phenylcarbonyl; or pharmaceutically acceptable salt, enantiomer or diastereomer thereof.

A further embodiment of present invention is (xv) a compound of formula (II) or (IIa), wherein $R^7$ and $R^8$ are independently selected from H, $C_{1-6}$alkyl and phenyl, said phenyl being unsubstituted or substituted with one to three substituents independently selected from $C_{1-6}$alkyl, halogen and $C_{1-6}$alkoxy; provided that $R^7$ and $R^8$ are not H simultaneously; or pharmaceutically acceptable salt, enantiomer or diastereomer thereof.

A further embodiment of present invention is (xvi) a compound of formula (II) or (IIa), wherein $R^7$ and $R^8$ are independently selected from H, methyl, ethyl, phenyl, chlorophenyl and methoxyphenyl; provided that $R^7$ and $R^8$ are not H simultaneously; or pharmaceutically acceptable salt, enantiomer or diastereomer thereof.

A further embodiment of present invention is (xvii) a compound of formula (II) or (IIa), wherein
$R^6$ is H, $C_{1-6}$alkylcarbonyl or $C_{1-6}$alkoxylcarbonyl;
$R^7$ and $R^8$ are independently selected from H and $C_{1-6}$alkyl, provided that $R^2$ and $R^3$ are not H simultaneously;
$R^9$ is $C_{1-6}$alkyl;
$R^{10}$ is H or $C_{1-6}$alkylcarbonyl;
or pharmaceutically acceptable salt, enantiomer or diastereomer thereof.

A further embodiment of present invention is (xviii) a compound of formula (II) or (IIa), wherein $R^6$ is H, acetyl, isopropylcarbonyl, tert-butylcarbonyl, isobutylcarbonyl or ethoxycarbonyl;
$R^7$ and $R^8$ are independently selected from H and methyl, provided that $R^7$ and $R^8$ are not H simultaneously;
$R^9$ is ethyl;
$R^{10}$ is H or acetyl;
or pharmaceutically acceptable salt, enantiomer or diastereomer thereof.

Another embodiment of present invention is that (xix) particular compounds of formula (II) or (IIa) are the following:
[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl] acetate;
[(1S)-1-[(2S,4S,5R)-5-(5-Amino-2-oxo-thiazolo[4,5-d]pyrimidin-3-yl)-4-[(1R)-1-hydroxyethyl]tetrahydrofuran-2-yl]propyl] acetate;
[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl] 2-methylpropanoate;
[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl] 2,2-dimethylpropanoate;
[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl] 3-methylbutanoate;
[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl] ethyl carbonate;
or pharmaceutically acceptable salt, enantiomer or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^{10}$ are as defined above unless otherwise indicated. Furthermore, and unless explicitly otherwise stated, all reactions, reaction conditions, abbreviations and symbols have the meanings well known to a person of ordinary skill in organic chemistry.

Scheme 1:

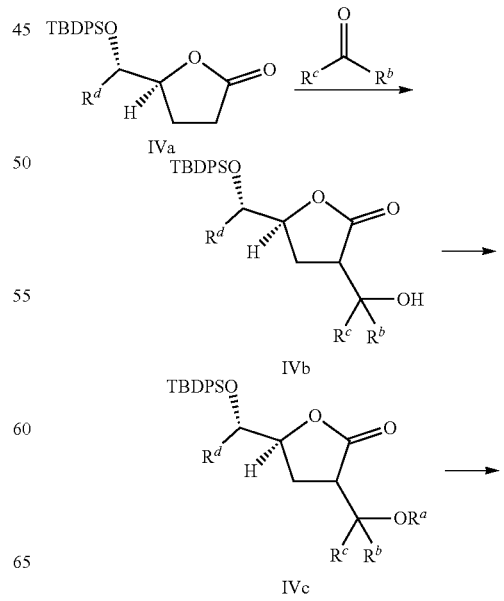

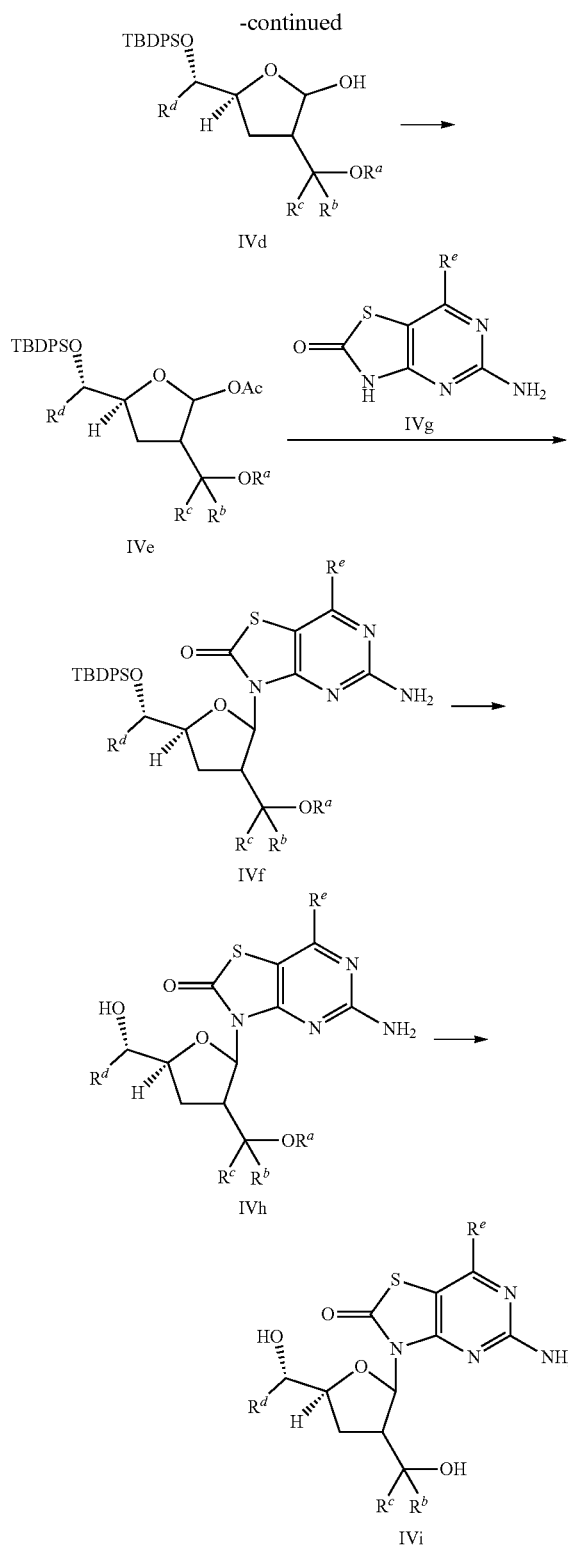

$R^a$ is $C_{1-6}$alkylcarbonyl, phenylcarbonyl or trimethylsilyl; $R^b$ is $R^2$ or $R^7$; $R^c$ is $R^3$ or $R^8$; $R^d$ is $R^4$ or $R^9$; $R^e$ is H or OH.

Compound IVi can be prepared according to Scheme 1. Aldol condensation of lactone IVa with aldehydes or ketones and a suitable base, such as lithium diisopropylamide and lithium bis(trimethylsilyl)azanide, affords compound IVb, and the reaction can also be carried out in the presence of Lewis acid additive such as zinc bromide and cerium(III) chloride. Compound IVc can be prepared by protection of hydroxyl group with protecting reagent, such as acetyl chloride, acetic anhydride, benzoyl chloride and trimethylsilyl chloride. Compound IVc can be converted to compound IVd through reduction by a reductant, such as diisobutyl aluminium hydride, followed by protection of newly generated hydroxy group with protecting reagent, such as acetyl chloride and acetic anhydride, to give the key intermediate IVe. Coupling of compound IVe with compound IVg in the presence of an appropriate silicon etherification agent, such as N,O-bis(trimethylsilyl)acetamide and hexamethyldisilazane, and a suitable Lewis acid, such as trimethylsilyl trifluoromethanesulfonate, trimethylsilyl iodide, tin(IV) chloride and titanium tetrachloride, affords compound IVf. Compound IVf can be converted to nucleoside analogues IVh by deprotection in the presence of an appropriate fluoride reagent such as tetrabutylammonium fluoride and ammonium fluoride. Compound IVh can be converted to final compound IVi by deprotection with a base, such as potassium carbonate and sodium methoxide.

Scheme 2:

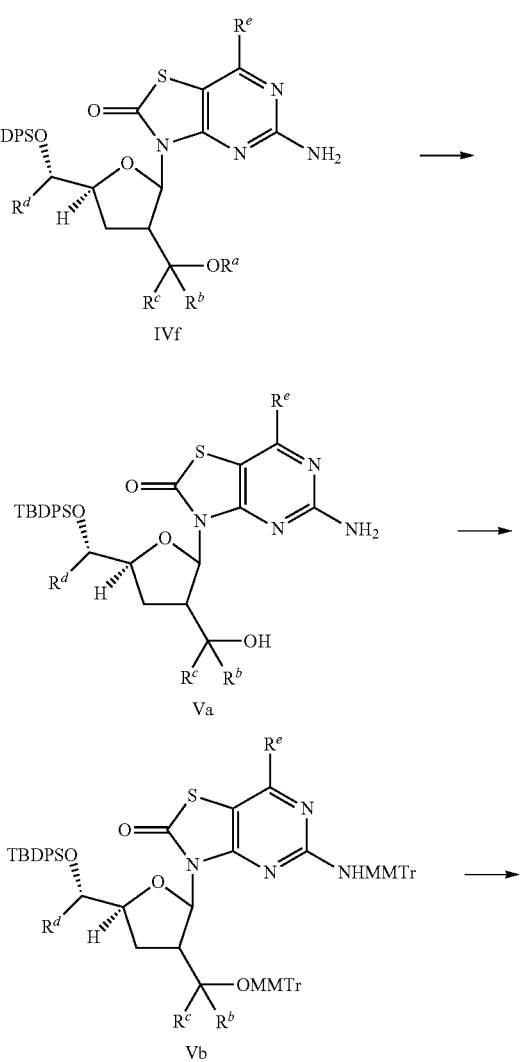

Scheme 3:

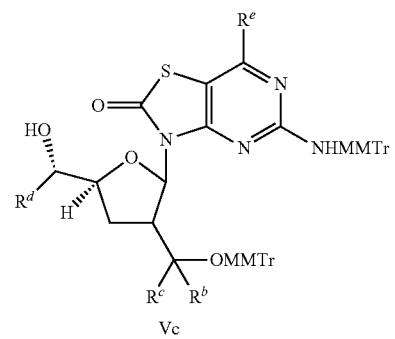
Vc

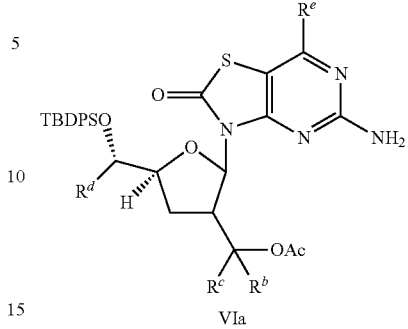
VIa

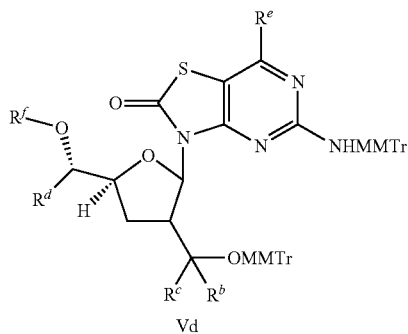
Vd

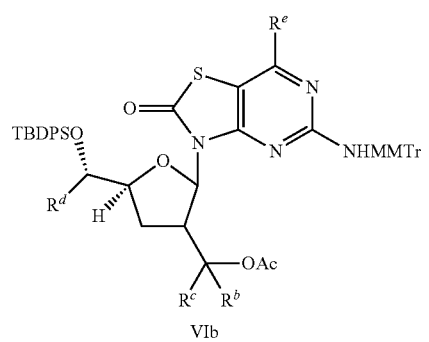
VIb

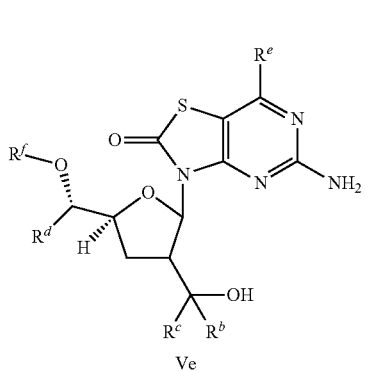
Ve

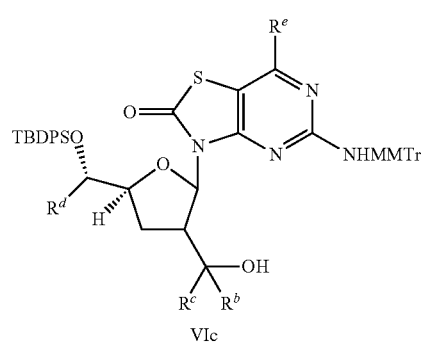
VIc $R^a$ is $C_{1-6}$alkylcarbonyl, phenylcarbonyl or trimethylsilyl; $R^b$ is $R^2$ or $R^7$; $R^c$ is $R^3$ or $R^8$; $R^d$ is $R^4$ or $R^9$; $R^e$ is H or OH; $R^f$ is $R^5$ or $R^{10}$.

Compound of interest Ve can be prepared according to Scheme 2. Selective deprotection of IVf in the presence of a suitable base such as potassium carbonate and sodium methoxide affords compound Va, which can be converted to compound Vb by introduction of 4-methoxytriphenylmethyl protecting group, followed by selective deprotection of tert-butyldiphenylsilyl in the presence of an appropriate fluoride reagent such as tetrabutylammonium fluoride and ammonium fluoride to give compound Vc. Compound Vd can be prepared by introduction of $R^f$ group, such as acetyl, and then deprotection of 4-methoxytriphenylmethyl groups of compound Vd with a suitable acid, such as formic acid, to give the final compound Ve.

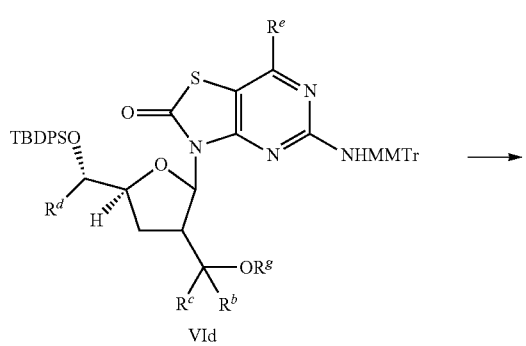
VId

-continued

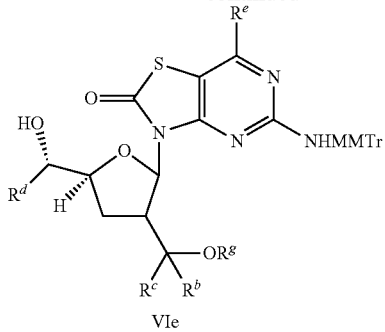

VIe

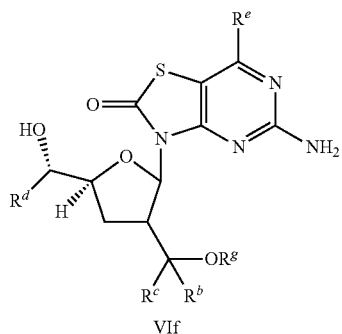

VIf $R^b$ is $R^2$ or $R^7$; R is $R^3$ or $R^8$; $R^d$ is $R^4$ or $R^9$; $R^e$ is H or OH; $R^g$ is $R^1$ or $R^6$.

Compound of interest VIf can be prepared according to Scheme 3. Compound VIa can be prepared in analogy to preparation of compound IVf in Scheme 1. Protection of amino group of compound VIa with 4-methoxytriphenylmethyl chloride affords compound VIb, which can be further converted to compound VIc by removing acetyl group with a base such as potassium carbonate and sodium methoxide. $R^g$ can be introduced into compound Vc in the corresponding reaction conditions to give compound VId, followed by deprotection of tert-butyldiphenylsilane in the presence of an appropriate fluoride reagent, such as tetrabutylammonium fluoride and ammonium fluoride, to give compound VIe. Compound VIe can be converted to final compound VIf by deprotection with a suitable acid such as formic acid.

This invention also relates to a process for the preparation of a compound of formula (I), (Ia), (II) or (IIa) comprising the reaction of:

(a) the reaction of a compound of formula (IVh),

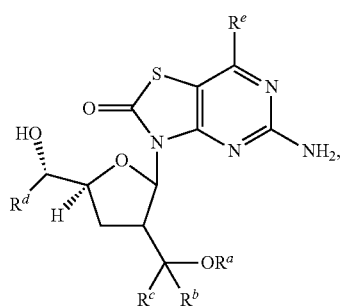

(IVh)

with a base, wherein $R^a$ is $C_{1-6}$alkylcarbonyl, phenylcarbonyl or trimethylsilyl; $R^b$ is $R^2$ or $R^7$; $R^c$ is $R^3$ or $R^8$; $R^d$ is $R^4$ or $R^9$; $R^e$ is H or OH;

(b) the reaction of a compound of formula (Vd),

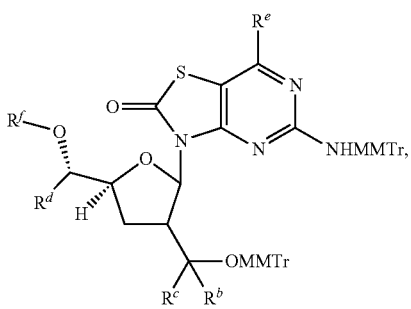

(Vd)

with an acid, wherein $R^b$ is $R^2$ or $R^7$; R is $R^3$ or $R^8$; $R^d$ is $R^4$ or $R^9$; $R^e$ is H or OH; $R^f$ is $R^5$ or $R^{10}$;

(c) the reaction of a compound of formula (VIe),

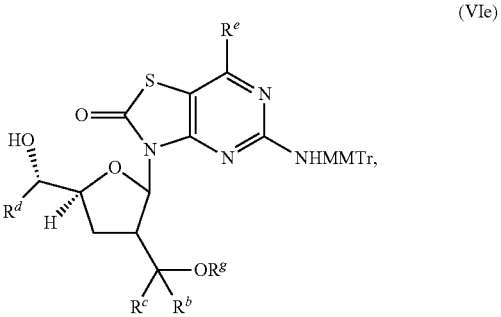

(VIe)

with an acid, wherein $R^b$ is $R^2$ or $R^7$; R is $R^3$ or R; $R^d$ is $R^4$ or $R^9$; $R^e$ is H or OH; $R^g$ is $R^1$ or $R^6$;

or wherein $R^a$, $R^b$, $R^c$, $R^d$, $R^e$, $R^f$, $R^g$, $R^1$ to $R^{10}$ are defined above.

In step (a), the base can be for example potassium carbonate and sodium methoxide.

In step (b) and (c), the acid can be for example formic acid.

A compound of formula (I), (Ia), (II) and (IIa) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) or (Ia) or their prodrugs may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) or (Ia) or their prodrugs are formulated in an acetate buffer, at pH 5. In another embodiment, the compounds of formula (I) or (Ia) or their prodrugs are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to activate TLR7 receptor and lead to produce INF-α and other cytokines, which can be used, but not limited, for the treatment or prevention of hepatitis B and/or C viral infected patients.

In one example, the pharmaceutically effective amount of the compound of the invention administered parenterally per dose will be in the range of about 0.1 to 50 mg/kg, alternatively about 0.1 to 30 mg/kg of patient body weight per day, with the typical initial range of compound used being 0.3 to 15 mg/kg/day. In another embodiment, oral unit dosage forms, such as tablets and capsules, preferably contain from about 20 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 20 to 1000 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 20 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I) or (Ia) or their prodrugs, formula (II) or (IIa), or pharmaceutically acceptable salts or enantiomers or diastereomers thereof.

In a further embodiment includes a pharmaceutical composition comprising a compound of formula (I) or (Ia) or their prodrugs, formula (II) or (IIa), or pharmaceutically acceptable salts or enantiomers or diastereomers thereof, together with a pharmaceutically acceptable carrier or excipient.

Another embodiment includes a pharmaceutical composition comprising a compound of formula (I) or (Ia) or their prodrugs, formula (II) or (IIa), or pharmaceutically acceptable salts or enantiomers or diastereomers thereof for use in the treatment of hepatitis B virus infection.

Indications and Methods of Treatment

The present invention provides methods for treating or preventing a hepatitis B viral infection and/or hepatitis C viral infection in a patient in need thereof.

The present invention further provides methods for introducing a therapeutically effective amount of a formula (I) or (Ia) compounds or their prodrugs, or other compounds of the invention into the blood stream of a patient in the treatment and/or prevention of hepatitis B and/or C viral infection.

The methods of the present invention are particularly well suited for human patients. In particular, the methods and doses of the present invention can be useful for, but not limited to, HBV and/or HCV infected patients. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Another embodiment includes a method of treating or preventing hepatitis B viral infection and/or hepatitis C viral infection in a mammal in need of such treatment, wherein the method comprises administering to said mammal a therapeutically effective amount of a compound of formula (I) or (Ia) or their prodrugs, or enantiomers, diastereomers, prodrugs or pharmaceutically acceptable salts thereof.

EXAMPLES

The invention will be more fully understood by reference to the following examples. They should not, however, be construed as limiting the scope of the invention.

Abbreviations

ACN: acetonitrile
BSA: N, O-bis(trimethylsilyl)acetamide
DIBAL-H: diisobutyl aluminium hydride
DMAP: 4-dimethylaminopyridine
DCM: dichloromethane
$EC_{50}$: the molar concentration of an agonist, which produces 50% of the maximum possible response for that agonist.

EtOAc: ethyl acetate
FBS: fetal bovine serum
HPLC: high performance liquid chromatography
LDA: lithium diisopropylamide
MMTrCl: 4-methoxytriphenylmethyl chloride
MS (ESI): mass spectroscopy (electron spray ionization)
obsd.: observed
SFC: supercritical fluid chromatography
TBAF: tetrabutylammonium fluoride
THF: tetrahydrofuran
TBDPSCl: tert-butylchlorodiphenylsilane
TMSOTf: trimethylsilyl trifluoromethanesulfonate
v/v: volume ratio General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 τm, OBD™ 30×100 mm) column or SunFire™ Perp $C_{18}$ (5 μm, OBD™ 30×100 mm) column.

Chiral Separation was conducted on Thar 350 preparative SFC using ChiralPak AD-10μ (200×50 mm I.D.) with mobile phase A for $CO_2$ and B for ethanol. LC/MS spectra were obtained using a Waters UPLC-SQD Mass. Standard LC/MS conditions were as follows (running time: 3 minutes):

Acidic condition: A: 0.1% formic acid and 1% acetonitrile in $H_2O$; B: 0.1% formic acid in acetonitrile;

Basic condition: A: 0.05% $NH_3.H_2O$ in $H_2O$; B: acetonitrile.

Mass spectra (MS): generally only ions which indicate the parent mass are reported, and unless otherwise stated the mass ion quoted is the positive mass ion $(M+H)^+$.

NMR Spectra were obtained using Bruker Avance 400 MHz.

All reactions involving air-sensitive reagents were performed under an argon atmosphere. Reagents were used as received from commercial suppliers without further purification unless otherwise noted.

Preparative Examples

Example 1

5-Amino-3-[(2R,3S,5S)-3-(1-hydroxyethyl)-5-(hydroxymethyl)tetrahydrofuran-2-yl]-6H-thiazolo[4,5-d]pyrimidine-2,7-dione

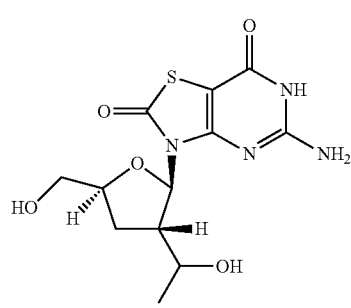

Preparation of (2S)-2-(hydroxymethyl)-2H-furan-5-one

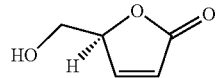

To a solution of ethyl (Z)-3-[(4S)-2,2-dimethyl-1,3-dioxolan-4-yl]prop-2-enoate (CAS #: 91926-90-8, commercially available from PharmaBlock (Nanjing) R&D Co. Ltd, 4.0 g, 20.0 mmol) in methanol was added catalytic amount of concentrated sulfuric acid (25 μL of 10% concentrated sulfuric acid in methanol). The mixture was stirred at room temperature for 2 hours. The resulting mixture was concentrated in vacuo and the residue was purified by flash column (eluting with 0-10% methanol in dichloromethane) to afford 2.25 g of (2S)-2-(hydroxymethyl)-2H-furan-5-one as a viscous oil.

Preparation of (2S)-2-[[tert-butyl(diphenyl)silyl]oxymethyl]-2H-furan-5-one

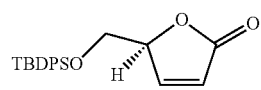

To a solution of 2.25 g of (2S)-2-(hydroxymethyl)-2H-furan-5-one (2.11 g, 16.0 mmol) and imidazole (1.63 g, 24.0 mmol) in dichloromethane was added tert-butyl-chlorodiphenyl-silane (5.2 mL, 20.0 mmol) dropwise. After being stirred at room temperature for 2 hours, the resulting mixture was washed with brine. The aqueous layer was extracted with dichloromethane. The organic layer was combined and washed with 1N hydrochloric acid, dried over $Na_2SO_4$ and concentrated in vacuo. The residue was purified by flash column (eluting with 0-30% EtOAc in petroleum ether) to afford 4.6 g of (2S)-2-[[tert-butyl(diphenyl)silyl]oxymethyl]-2H-furan-5-one as a white solid.

Preparation of (5S)-5-[[tert-butyl(diphenyl)silyl]oxymethyl]tetrahydrofuran-2-one

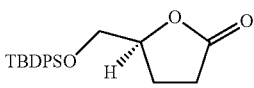

A solution of (2S)-2-[[tert-butyl(diphenyl)silyl]oxymethyl]-2H-furan-5-one (2.8 g, 8.0 mmol) in EtOAc (40 mL) was stirred with 10% palladium on carbon (280 mg) under hydrogen atmosphere overnight. The resulting mixture was filtered and the filtrate was concentrated in vacuo to afford 2.7 g of (5S)-5-[[tert-butyl(diphenyl)silyl]oxymethyl]tetrahydrofuran-2-one as a viscous oil.

Preparation of (5S)-5-[[tert-butyl(diphenyl)silyl]oxymethyl]-3-(1-hydroxyethyl)tetrahydrofuran-2-one

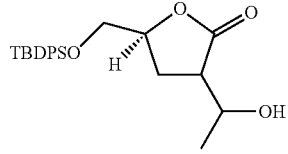

1d

To a solution of (5S)-5-[[tert-butyl(diphenyl)silyl]oxymethyl]tetrahydrofuran-2-one (10 g, 28 mmol) in THF (150 mL) was added LDA (42 mL, 84 mmol) slowly at −78° C. and stirred under $N_2$ for 2 hours, followed by addition of $CH_3CHO$ (2.46 g, 56 mmol) and stirred for another 2 hours. The reaction mixture was quenched by addition of saturate solution of $NH_4Cl$ (200 mL), and then extracted with EtOAc (500 mL). The organic layer was washed with brine (200 mL) and concentrated in vacuo. The residue was purified by flash column (eluting with 0-6% EtOAc in petroleum ether) to afford 4 g of (5S)-5-[[tert-butyl(diphenyl)silyl]oxymethyl]-3-(1-hydroxyethyl)tetrahydrofuran-2-one as a yellow oil.

Preparation of 1-[(5S)-5-[[tert-butyl(diphenyl)silyl]oxymethyl]-2-oxo-tetrahydrofuran-3-yl]ethyl benzoate

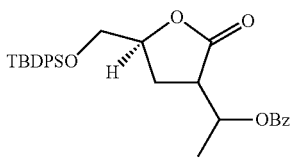

1e

To a solution of (5S)-5-[[tert-butyl(diphenyl)silyl]oxymethyl]-3-(1-hydroxyethyl)tetrahydrofuran-2-one (7 g, 17.5 mmol) in pyridine (50 mL) was added DMAP (100 mg, 0.82 mmol) at 0° C., followed by addition of benzoyl chloride (3.7 g, 26.3 mmol). The mixture was stirred at 20° C. under $N_2$ for 12 hours and then diluted with EtOAc (500 mL), washed with brine (300 mL). The organic layer was dried over $Na_2SO_4$ and concentrated in vacuo. The residue was purified by column chromatography on silica gel (eluting with 0-5% EtOAc in petroleum ether) to give 8 g of 1-[(5S)-5-[[tert-butyl(diphenyl)silyl]oxymethyl]-2-oxo-tetrahydrofuran-3-yl]ethyl benzoate as an oil.

Preparation of 1-[(5S)-5-[[tert-butyl(diphenyl)silyl]oxymethyl]-2-hydroxy-tetrahydrofuran-3-yl]ethyl benzoate

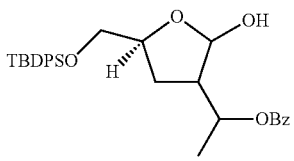

1f

To a solution of 1-[(5S)-5-[[tert-butyl(diphenyl)silyl]oxymethyl]-2-oxo-tetrahydrofuran-3-yl]ethyl benzoate (3 g, 6 mmol) in toluene (50 mL) was added DIBAL-H (7.8 mL, 7.8 mmol) slowly at −78° C. After being stirred at −78° C. under $N_2$ for 2 hours, the reaction was quenched with 1N HCl solution (20 mL), and extracted with EtOAc (300 mL). The organic layer was washed with saturate solution of $NaHCO_3$ (100 mL), brine (100 mL) and dried over $Na_2SO_4$. The solvent was concentrated in vacuo to give 2.8 g of 1-[(5S)-5-[[tert-butyl(diphenyl)silyl]oxymethyl]-2-hydroxy-tetrahydrofuran-3-yl]ethyl benzoate as the crude product which was used for the next step directly.

Preparation of 1-[(5S)-2-acetoxy-5-[[tert-butyl(diphenyl)silyl]oxymethyl]tetrahydrofuran-3-yl]ethyl benzoate

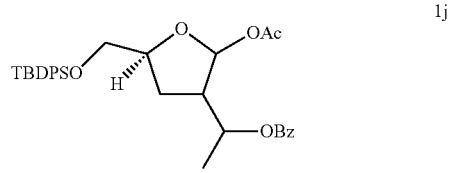

1j

To a solution of 1-[(5S)-5-[[tert-butyl(diphenyl)silyl]oxymethyl]-2-hydroxy-tetrahydrofuran-3-yl]ethyl benzoate (2.8 g, 5.5 mmol) in pyridine (20 mL) was added $Ac_2O$ (1.7 g, 16.5 mmol) and DMAP (130 mg, 1.1 mmol). After being stirred at 25° C. under $N_2$ for 12 hours, the reaction mixture was diluted with EtOAc (300 mL), and washed with brine (100 mL). The solvent was concentrated in vacuo to give the residue which was purified by column chromatography on silica gel (eluting with 0-5% EtOAc in petroleum ether) to give 2.4 g of 1-[(5S)-2-acetoxy-5-[[tert-butyl(diphenyl)silyl]oxymethyl]tetrahydrofuran-3-yl]ethyl benzoate as an oil.

Preparation of 1-[(5S)-2-(5-amino-2,7-dioxo-6H-thiazolo[4,5-d]pyrimidin-3-yl)-5-[[tert-butyl(diphenyl)silyl]oxymethyl]tetrahydrofuran-3-yl]ethyl benzoate

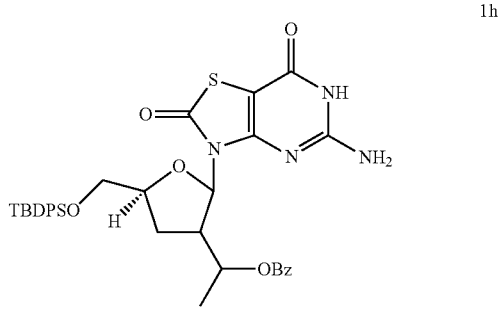

1h

To a suspension of 5-amino-3,6-dihydrothiazolo[4,5-d]pyrimidine-2,7-dione (0.9 g, 4.94 mmol, CAS: 30161-97-8, WuXi AppTec) in $CH_3CN$ (60 mL) was added BSA (1.67 g, 8.25 mmol). After being stirred at 90° C. under $N_2$ for 3 hours, 1-[(5S)-2-acetoxy-5-[[tert-butyl(diphenyl)silyl]oxymethyl]tetrahydrofuran-3-yl]ethyl benzoate (0.9 g, 1.65 mmol) was added, followed by addition of TMSOTf (3 g, 13.2 mmol) at 0° C. under $N_2$. After being stirred at 0 to 20° C. for 2 hours, the reaction was quenched with saturate solution of $NaHCO_3$, and extracted with EtOAc (300 mL).

The organic layer was washed with brine (100 mL) and concentrated in vacuo to give the residue which was purified by column chromatography on silica gel (eluting with 1:50 methanol in DCM) to give 0.9 g of 1-[(5S)-2-(5-amino-2,7-dioxo-6H-thiazolo[4,5-d]pyrimidin-3-yl)-5-[[tert-butyl(diphenyl)silyl]oxymethyl]tetrahydrofuran-3-yl]ethyl benzoate as a white solid.

Preparation of 5-amino-3-[(2R,3S,5S)-3-(1-hydroxyethyl)-5-(hydroxymethyl)tetrahydrofuran-2-yl]-6H-thiazolo[4,5-d]pyrimidine-2,7-dione

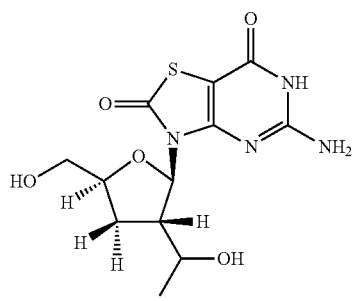

1

To a solution of 1-[(5S)-2-(5-amino-2,7-dioxo-6H-thiazolo[4,5-d]pyrimidin-3-yl)-5-[[tert-butyl(diphenyl)silyl]oxymethyl]tetrahydrofuran-3-yl]ethyl benzoate (1 g, 1.5 mmol) in MeOH (60 mL) was added $NH_4F$ (0.55 g, 15 mmol) and the mixture was stirred at 80° C. under $N_2$ for 3 hours. The reaction mixture was evaporated and then dissolved in EtOAc (100 mL), washed with brine (50 mL) and the solvent was concentrated in vacuo to give the residue which was purified by column chromatography on silica gel (eluting with 1:100 methanol in DCM) to give 0.5 g of crude product. Further purification by preparative HPLC gives two intermediates, 150 mg of Intermediate A and 120 mg of Intermediate B. Both of them were treated with $K_2CO_3$ (To intermediate A: 97 mg, 0.7 mmol and to intermediate B: 77 mg, 0.56 mmol) in methanol (15 mL) at 40° C. under $N_2$ for 12 hours respectively. The methanol was evaporated in vacuo and the residue was purified by preparative HPLC to give Example 1-A and Example 1-B.

The stereochemistry of Example 1 on ribose ring was established by 2D NMR NOESY experiments. As shown in below, correlations of $C^5{}'H$ with $C^3{}'H^a$, $C^4{}'H$ with $C^3{}'H^b$, $C^2{}'H$ with $C^3{}'H^a$, $C^1{}'H$ with $C^4{}'H$, $C^3{}'H^b$ with $C^6{}'H$ were observed.

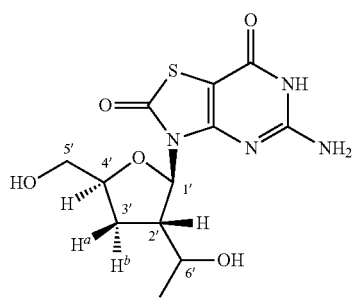

1

Example 1-A: 35.3 mg as a white solid. MS obsd. (ESI+) [(M+H)+]: 328.9. $^1H$ NMR (400 MHz, Methanol-$d_4$) δ ppm: 1.20 (d, J=6.40 Hz, 3H), 1.90-2.00 (m, 1H), 2.33 (ddd, J=12.55, 9.79, 6.78 Hz, 1H), 3.02-3.15 (m, 1H), 3.63-3.84 (m, 3H), 4.16-4.25 (m, 1H), 6.24 (d, J=5.90 Hz, 1H).

Example 1-B: 30.2 mg as a white solid. MS obsd. (ESI+) [(M+H)+]: 329.0. $^1H$ NMR (400 MHz, Methanol-$d_4$) δ ppm: 1.18 (d, J=6.27 Hz, 3H), 2.07-2.21 (m, 1H), 2.25-2.35 (m, 1H), 3.02-3.11 (m, 1H), 3.63-3.75 (m, 2H), 3.76-3.86 (m, 1H), 4.17-4.24 (m, 1H), 6.12 (d, J=6.02 Hz, 1H).

Example 2

5-Amino-3-[(2R,3S,5S)-3-[cyclopropyl(hydroxy)methyl]-5-(hydroxymethyl)tetrahydrofuran-2-yl]-6H-thiazolo[4,5-d]pyrimidine-2,7-dione

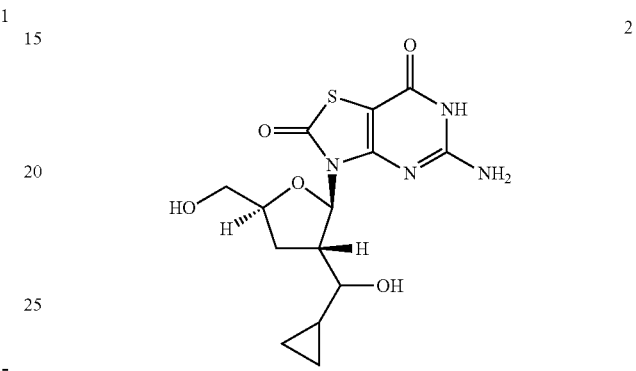

2

The title compound was prepared in analogy to Example 1, by using cyclopropanecarbaldehyde instead of acetaldehyde. Example 2 was purified by preparative HPLC and SFC to afford Example 2-A and Example 2-B as a white solid.

Example 2-A: MS obsd. (ESI+) [(M+H)+]: 355.0. $^1H$ NMR (400 MHz, Methanol-$d_4$) δ ppm: 0.22-0.30 (m, 1H), 0.30-0.38 (m, 1H), 0.38-0.53 (m, 2H), 0.82-0.95 (m, 1H), 2.16-2.27 (m, 1H), 2.33 (ddd, J=12.61, 9.41, 6.34 Hz, 1H), 2.92 (dd, J=8.28, 5.52 Hz, 1H), 3.25-3.29 (m, 1H), 3.36-3.44 (m, 1H), 3.63-3.77 (m, 2H), 4.24 (quin, J=5.99 Hz, 1H), 6.19 (d, J=6.53 Hz, 1H).

Example 2-B: MS obsd. (ESI+) [(M+H)+]: 354.9. $^1H$ NMR (400 MHz, Methanol-$d_4$) δ ppm: 0.20-0.30 (m, 1H), 0.30-0.37 (m, 1H), 0.42-0.52 (m, 2H), 0.81-0.97 (m, 1H), 2.02-2.16 (m, 1H), 2.35 (ddd, J=12.55, 9.79, 6.65 Hz, 1H), 2.95 (dd, J=8.22, 6.09 Hz, 1H), 3.62-3.78 (m, 2H), 4.22 (t, J=5.96 Hz, 1H), 6.29 (d, J=6.27 Hz, 1H).

Example 3

5-Amino-3-[(2R,3S,5S)-5-(hydroxymethyl)-3-(1-hydroxypropyl)tetrahydrofuran-2-yl]-6H-thiazolo[4,5-d]pyrimidine-2,7-dione

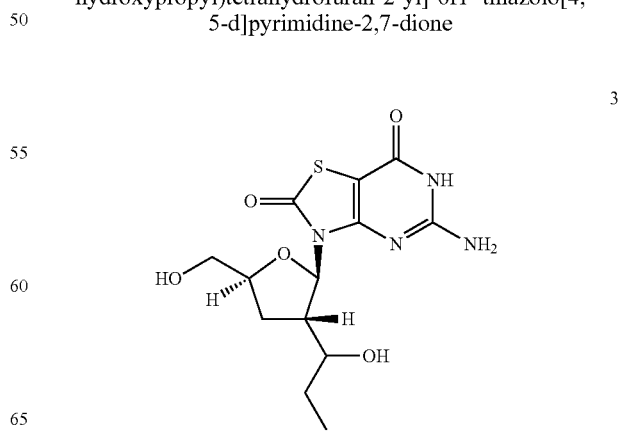

3

The title compound was prepared in analogy to Example 1, by using propionaldehyde instead of acetaldehyde. Example 3 was purified by preparative HPLC to afford Example 3-A and Example 3-B as white solid.

Example 3-A: MS obsd. (ESI$^+$) [(M+H)$^+$]: 355.0. $^1$H NMR (400 MHz, Methanol-d$_4$) δ ppm: 0.95 (t, J=7.40 Hz, 3H), 1.36-1.57 (m, 2H), 2.08-2.36 (m, 2H), 3.08-3.23 (m, 1H), 3.46-3.55 (m, 1H), 3.62-3.77 (m, 2H), 4.21 (t, J=11.86 Hz, 1H), 6.14 (d, J=6.40 Hz, 1H).

Example 3-B: MS obsd. (ESI$^+$) [(M+H)$^+$]: 355.0. $^1$H NMR (400 MHz, Methanol-d$_4$) δ ppm: 0.93 (t, J=7.40 Hz, 3H), 1.36-1.48 (m, 1H), 1.47-1.59 (m, 1H), 1.97 (ddd, J=12.45, 7.69, 6.46 Hz, 1H), 2.32 (ddd, J=12.42, 9.79, 6.65 Hz, 1H), 3.08-3.21 (m, 1H), 3.48-3.58 (m, 1H), 3.60-3.78 (m, 2H), 4.13-4.28 (m, 1H), 6.23 (d, J=6.15 Hz, 1H).

Example 4

5-Amino-3-[(2R,3S,5S)-5-(hydroxymethyl)-3-[hydroxy(phenyl)methyl]tetrahydrofuran-2-yl]-6H-thiazolo[4,5-d]pyrimidine-2,7-dione

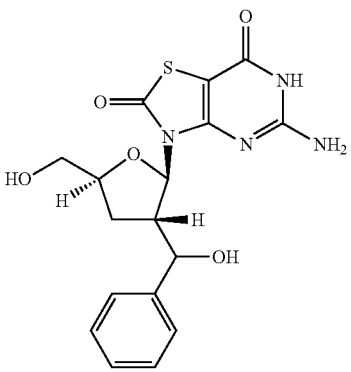

4

The title compound was prepared in analogy to Example 1, by using benzaldehyde instead of acetaldehyde. Example 4 was purified by preparative HPLC to afford Example 4-A and Example 4-B as white solid.

Example 4-A: MS obsd. (ESI$^+$) [(M+H)$^+$]: 391.1; $^1$H NMR (400 MHz, Methanol-d$_4$) δ ppm: 2.26 (dt, J=12.89, 8.49 Hz, 1H), 2.40 (ddd, J=13.02, 8.75, 4.45 Hz, 1H), 3.57-3.81 (m, 3H), 4.21 (dq, J=8.75, 4.40 Hz, 1H), 4.54 (d, J=8.41 Hz, 1H), 5.92 (d, J=7.91 Hz, 1H), 7.08-7.15 (m, 1H), 7.19 (t, J=7.28 Hz, 2H), 7.24-7.31 (m, 2H).

Example 4-B: MS obsd. (ESI$^+$) [(M+H)$^+$]: 391.0; $^1$H NMR (400 MHz, Methanol-d$_4$) δ ppm: 1.98-2.25 (m, 2H), 3.53-3.78 (m, 3H), 4.19 (dt, J=11.58, 5.82 Hz, 1H), 4.70-4.88 (m, 1H), 6.26 (d, J=6.78 Hz, 1H), 7.09-7.19 (m, 1H), 7.20-7.28 (m, 1H), 7.34 (d, J=7.53 Hz, 1H).

Example 5

5-Amino-3-[(2R,3S,5S)-3-[hydroxy-(2-methoxyphenyl)methyl]-5-(hydroxymethyl)tetrahydrofuran-2-yl]-6H-thiazolo[4,5-d]pyrimidine-2,7-dione

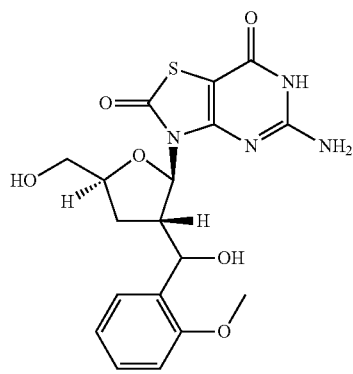

5

The title compound was prepared in analogy to Example 1, by using 2-methoxybenzaldehyde instead of acetaldehyde. Example 5 was purified by preparative HPLC to afford Example 5-A and Example 5-B as a white solid.

Example 5-A: MS obsd. (ESI$^+$) [(M+H)$^+$]: 421.1; $^1$H NMR (400 MHz, Methanol-d$_4$) δ ppm: 2.18-2.35 (m, 2H), 3.59-3.74 (m, 2H), 3.76 (s, 3H), 3.88 (quin, J=8.31 Hz, 1H), 4.17-4.30 (m, 1H), 4.94 (d, J=7.65 Hz, 1H), 5.94 (d, J=7.91 Hz, 1H), 6.73-6.87 (m, 2H), 7.11 (td, J=7.81, 1.69 Hz, 1H), 7.25-7.34 (m, 1H).

Example 5-B: MS obsd. (ESI$^+$) [(M+H)$^+$]: 421.1; $^1$H NMR (400 MHz, Methanol-d$_4$) δ ppm: 2.07-2.36 (m, 2H), 3.57-3.73 (m, 2H), 3.78 (s, 3H), 3.82-3.96 (m, 1H), 4.15-4.33 (m, 1H), 5.12 (d, J=4.77 Hz, 1H), 6.19 (d, J=7.28 Hz, 1H), 6.74-6.87 (m, 2H), 7.01-7.15 (m, 1H), 7.39-7.50 (m, 1H).

Example 6

5-Amino-3-[(2R,3S,5S)-3-[(2-chlorophenyl)-hydroxy-methyl]-5-(hydroxymethyl)tetrahydrofuran-2-yl]-6H-thiazolo[4,5-d]pyrimidine-2,7-dione

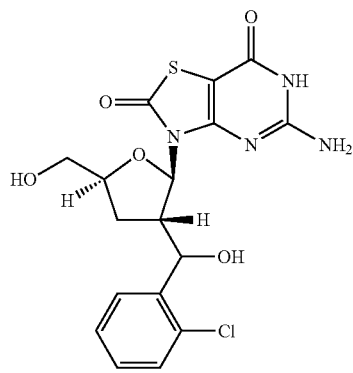

6

The title compound was prepared in analogy to Example 1, by using 2-chlorobenzaldehyde instead of acetaldehyde. Example 6 was purified by preparative HPLC to afford Example 6-A and Example 6-B as a white solid.

Example 6-A: MS obsd. (ESI$^+$) [(M+H)$^+$]: 425.1; $^1$H NMR (400 MHz, Methanol-d$_4$) δ ppm: 2.14 (ddd, J=12.71, 9.19, 5.21 Hz, 1H), 2.32 (dt, J=12.67, 8.16 Hz, 1H), 3.54-3.79 (m, 3H), 4.18-4.35 (m, 1H), 5.13 (d, J=5.90 Hz, 1H), 6.10 (d, J=7.53 Hz, 1H), 7.10-7.21 (m, 1H), 7.22-7.32 (m, 2H), 7.53 (dd, J=7.72, 1.44 Hz, 1H).

Example 6-B: MS obsd. (ESI$^+$) [(M+H)$^+$]: 425.1; $^1$H NMR (400 MHz, Methanol-d$_4$) δ ppm: 2.12-2.35 (m, 2H); 3.57-3.76 (m, 2H); 3.80-3.97 (m, 1H), 4.14-4.33 (m, 1H), 5.20 (d, J=4.77 Hz, 1H), 6.29 (d, J=6.90 Hz, 1H), 7.07-7.21 (m, 2H), 7.23-7.29 (m, 1H), 7.49-7.73 (m, 1H).

Example 7

5-Amino-3-[(2R,3S,5S)-5-(hydroxymethyl)-3-[(S)-hydroxy(2-pyridyl)methyl]tetrahydrofuran-2-yl]-6H-thiazolo[4,5-d]pyrimidine-2,7-dione

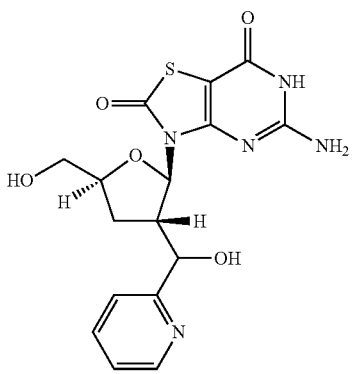

7

The title compound was prepared in analogy to Example 1, by using pyridine-2-carbaldehyde instead of acetaldehyde. Example 7 was purified by preparative HPLC to afford Example 7 as a white solid.

Example 7: MS obsd. (ESI$^+$) [(M+H)$^+$]: 391.9; $^1$H NMR (400 MHz, Methanol-d$_4$) δ ppm: 2.21 (t, J=7.59 Hz, 2H), 3.58-3.76 (m, 3H), 4.17-4.33 (m, 1H), 4.75 (d, J=6.15 Hz, 1H), 6.15 (d, J=6.78 Hz, 1H), 7.24 (dd, J=6.71, 5.21 Hz, 1H), 7.55 (d, J=7.91 Hz, 1H), 7.79 (td, J=7.72, 1.51 Hz, 1H), 8.38 (d, J=4.89 Hz, 1H).

Example 8

5-Amino-3-[(2R,3S,5S)-5-(hydroxymethyl)-3-(1-hydroxy-1-methyl-ethyl)tetrahydrofuran-2-yl]-6H-thiazolo[4,5-d]pyrimidine-2,7-dione

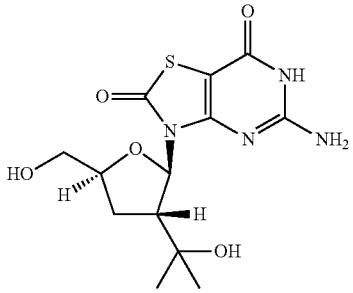

8

Preparation of (3S,5S)-5-[[tert-butyl(diphenyl)silyl]oxymethyl]-3-(1-hydroxy-1-methyl-ethyl)tetrahydrofuran-2-one (Compound 8a)

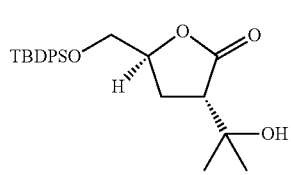

8a

To a cooled solution of (5S)-5-[[tert-butyl(diphenyl)silyl]oxymethyl]tetrahydrofuran-2-one (Compound 1d, 5.00 g, 14.0 mmol) in dry tetrahydrofuran (28 mL) was added a solution of lithium bis(trimethylsilyl)azanide (11.8 mL, 1.3 M, 15.4 mmol) in tetrahydrofuran dropwise at −78° C. under argon. After the addition, the mixture was stirred at −78° C. for 1 hour. Then distilled acetone (1.23 mL, 15.4 mmol) was added dropwise to the mixture and the resulting mixture was stirred further at −78° C. for 2 hours. The reaction was quenched by addition of saturated aqueous solution of NH$_4$Cl and the mixture was extracted with EtOAc (30 mL) three times. The combined organic layer was dried over Na$_2$SO$_4$ and concentrated in vacuo. The residue was purified by flash column (eluting with 0-30% ethyl acetate in petroleum ether) to afford 5.70 g of (3S,5S)-5-[[tert-butyl(diphenyl)silyl]oxymethyl]-3-(1-hydroxy-1-methyl-ethyl)tetrahydrofuran-2-one as a light yellow solid.

Preparation of (3S,5S)-5-[[tert-butyl(diphenyl)silyl]oxymethyl]-3-(1-methyl-1-trimethylsilyloxy-ethyl)tetrahydrofuran-2-one (Compound 8b)

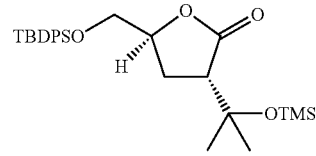

8b

To a solution of (3S,5S)-5-[[tert-butyl(diphenyl)silyl]oxymethyl]-3-(1-hydroxy-1-methyl-ethyl)tetrahydrofuran-2-one (Compound 8a, 1.65 g, 4.0 mmol) and N-ethyl-N-propan-2-ylpropan-2-amine (1.25 mL, 7.2 mmol) in dichloromethane (20 mL) was added trimethylsilyl chloride (0.76 mL, 6.0 mmol). The resulting mixture was stirred at room temperature overnight and concentrated in vacuo. The residue was purified by flash column (eluting with 0-20% ethyl acetate in petroleum ether) to afford 950 mg of (3S,5S)-5-[[tert-butyl(diphenyl)silyl]oxymethyl]-3-(1-methyl-1-trimethylsilyloxy-ethyl)tetrahydrofuran-2-one.

Preparation of [(3S,5S)-5-[[tert-butyl(diphenyl)silyl]oxymethyl]-3-(1-methyl-1-trimethylsilyloxy-ethyl)tetrahydrofuran-2-yl] acetate (Compound 8c)

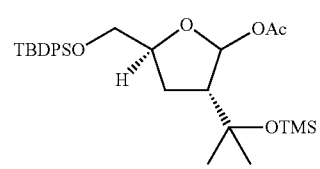

8c

The title compound was prepared in analogy to Compound 1j in Example 1, by using (3S,5S)-5-[[tert-butyl(diphenyl)silyl]oxymethyl]-3-(1-methyl-1-trimethylsilyloxy-ethyl)tetrahydrofuran-2-one instead of 1-[(5S)-5-[[tert-butyl(diphenyl)silyl]oxymethyl]-2-oxo-tetrahydrofuran-3-yl]ethyl (Compound 1e).

Preparation of 5-amino-3-[(2R,3S,5S)-5-[[tert-butyl(diphenyl)silyl]oxymethyl]-3-(1-hydroxy-1-methyl-ethyl)tetrahydrofuran-2-yl]-6H-thiazolo[4,5-d]pyrimidine-2,7-dione (Compound 8d)

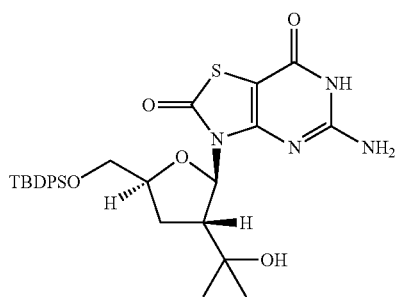

8d

A mixture of 5-amino-3,6-dihydrothiazolo[4,5-d]pyrimidine-2,7-dione (276 mg, 1.50 mmol) and bis(trimethylsilyl)acetamide (1.11 mL, 4.5 mmol) was heated with stirring at 75° C. under argon until the mixture became clear. The mixture was cooled to room temperature and then to the mixture [(3S,5S)-5-[[tert-butyl(diphenyl)silyl]oxymethyl]-3-(1-methyl-1-trimethylsilyloxy-ethyl)tetrahydrofuran-2-yl] acetate (Compound 8c, 396 mg, 0.75 mmol) and trimethylsilyltrifluoromethanesulfonate (500 µL, 2.25 mmol) were introduced. The resulting mixture was heated at 75° C. under argon for 3 hours. The resulting mixture was concentrated in vacuo to remove the solvent and the residue was purified by flash column (eluting with 0-5% methanol in dichloromethane) to afford 58 mg of 5-amino-3-[(2R,3S,5S)-5-[[tert-butyl(diphenyl)silyl]oxymethyl]-3-(1-hydroxy-1-methyl-ethyl)tetrahydrofuran-2-yl]-6H-thiazolo[4,5-d]pyrimidine-2,7-dione as a brown solid.

Preparation of 5-amino-3-[(2R,3S,5S)-5-(hydroxymethyl)-3-(1-hydroxy-1-methyl-ethyl)tetrahydrofuran-2-yl]-6H-thiazolo[4,5-d]pyrimidine-2,7-dione (Example 8)

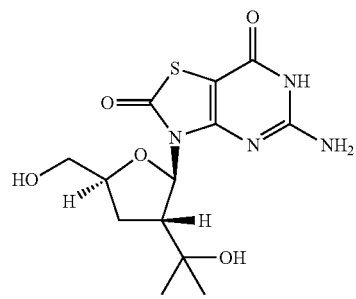

8

The title compound was prepared in analogy to Example 1, by using 5-amino-3-[(2R,3S,5S)-5-[[tert-butyl(diphenyl)silyl]oxymethyl]-3-(1-hydroxy-1-methyl-ethyl)tetrahydrofuran-2-yl]-6H-thiazolo[4,5-d]pyrimidine-2,7-dione (Compound 8d) instead of 1-[(5S)-2-(5-amino-2,7-dioxo-6H-thiazolo[4,5-d]pyrimidin-3-yl)-5-[[tert-butyl(diphenyl)silyl]oxymethyl]tetrahydrofuran-3-yl]ethyl benzoate.

Example 8: MS obsd. (ESI⁺) [(M+H)⁺]: 343.0. ¹H NMR (400 MHz, Methanol-d₄) δ ppm: 1.20 (s, 3H), 1.25 (s, 3H), 2.13 (ddd, J=12.89, 7.69, 5.65 Hz, 1H), 2.21-2.40 (m, 1H), 2.99-3.20 (m, 1H), 3.60-3.81 (m, 2H), 4.18 (ddd, J=12.33, 7.37, 5.14 Hz, 1H), 6.27 (d, J=6.02 Hz, 1H).

Example 9

[(1R)-1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]ethyl] acetate (Example 9-A) and [(1S)-1-[(2R,3S,5S)-2-(5-amino-2,7-dioxo-6H-thiazolo[4,5-d]pyrimidin-3-yl)-5-[(1S)-1-hydroxypropyl]tetrahydrofuran-3-yl]ethyl] acetate (Example 9-B)

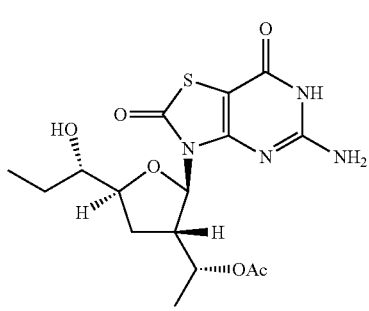

9-A

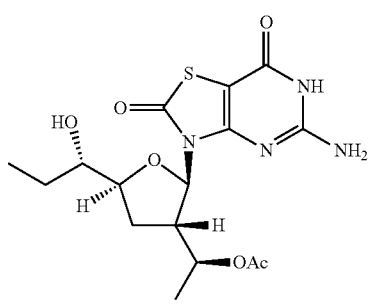

9-B

Preparation of (2S)-5-oxotetrahydrofuran-2-carboxylic acid

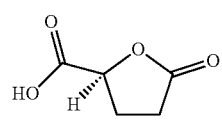

9a (2S)-2-Aminopentanedioic acid (2.50 kg, 16.99 mol) was dissolved in H₂O (6 L) and concentrated HCl (3.5 L), then a solution of NaNO₂ (1.76 kg, 25.49 mol) in H₂O (5 L) was added slowly at −5° C. to 0° C. After being stirred at 28° C. for 16 hours, the reaction mixture was concentrated below 50° C. to give a residue, which was treated with EtOAc (5 L). After being filtered, the filtrate was dried over Na₂SO₄ and concentrated in vacuo to give 1.5 kg of (2S)-5-oxotetrahydrofuran-2-carboxylic acid as a colorless oil which was used for the next step without further purification.

Preparation of (2S)-5-oxotetrahydrofuran-2-carbonyl chloride

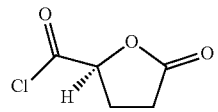

To a mixture of (2S)-5-oxotetrahydrofuran-2-carboxylic acid (1.00 kg, 7.69 mol) in DCM (10.00 L) and DMF (10.00 mL) was added (COCl)$_2$ (2.93 kg, 23.06 mol) dropwise slowly at 0° C. under N$_2$. The reaction was stirred at 0° C. for 30 minutes, then heated to 25° C. and stirred for additional 2 hours. After the reaction was completed, the mixture was concentrated in vacuo at 40° C. to afford 1.0 kg of (2S)-5-oxotetrahydrofuran-2-carbonyl chloride as a yellow oil which was used for the next step directly.

Preparation of (5S)-5-propanoyltetrahydrofuran-2-one

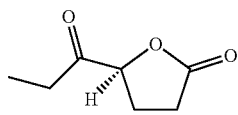

To a solution of (2S)-5-oxotetrahydrofuran-2-carbonyl chloride (1.00 kg, 6.73 mol) in THF (5.00 L) was added bromo(ethyl)magnesium (2243 mL, 6.73 mol) dropwise at −78° C. under N$_2$. After the addition, the mixture was stirred at this temperature for 3 hours. The mixture was poured into saturated NH$_4$Cl (100 mL), extracted with EtOAc, dried over Na$_2$SO$_4$, filter and concentrated in vacuo. The residue was purified by column chromatography on silica gel (eluting with 10-50% EtOAc in petroleum ether) to give 500 g of (5S)-5-propanoyltetrahydrofuran-2-one as a light yellow oil.

Preparation of (5S)-5-[(1S)-1-hydroxypropyl]tetrahydrofuran-2-one

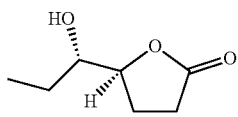

To a solution of (5S)-5-propanoyltetrahydrofuran-2-one (1.50 kg, 10.55 mol) in THF (15.00 L) was added dropwise K-selectride (2.34 kg, 10.55 mol) at −78° C. under N$_2$. The reaction was stirred at −78° C. for 3 hours until TLC showed the reaction was completed. The resulting mixture was poured into a cold aqueous NaHCO$_3$ (15 L) and stirred for 12 hours. The aqueous phase was extracted with EtOAc (10 L) four times. The combined organic phase was washed with brine (5 L), dried with anhydrous Na$_2$SO$_4$, filtered and concentrated in vacuo. The residue was purified by silica gel chromatography (eluting with 0-30% EtOAc in petroleum ether) to afford 500 g of (5S)-5-[(1S)-1-hydroxypropyl]tetrahydrofuran-2-one as a yellow oil. (Refer to *Eur. J. Med. Chem.* 1997, 32, 617-623)

Preparation of (5S)-5-[(1S)-1-[tert-butyl(diphenyl)silyl]oxypropyl]tetrahydrofuran-2-one

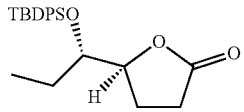

To a mixture of (5S)-5-[(1S)-1-hydroxypropyl]tetrahydrofuran-2-one (500.00 g, 3.47 mol) and imidazole (708 g, 10.4 mol) in DMF (8.0 L) was added TBDPSCl (1.43 kg, 5.2 mol) dropwise at 0° C. under N$_2$. After being stirred at 25° C. for 12 hours, the mixture was diluted with water (120 mL) and extracted with EtOAc (50 mL) three times. The combined organic phase was washed with brine (30 mL), dried over anhydrous Na$_2$SO$_4$, filtered and concentrated in vacuo. The residue was purified by silica gel chromatography (eluting with 30-50% EtOAc in petroleum ether) to afford 860 g of (5S)-5-[(1S)-1-[tert-butyl(diphenyl)silyl]oxypropyl]tetrahydrofuran-2-one as a white solid.

Compound 9e: $^1$H NMR (400 MHz, CDCl$_3$) δ ppm: 0.76 (t, J=7.47 Hz, 3H), 1.08 (s, 9H), 1.36-1.52 (m, 1H), 1.61-1.75 (m, 1H), 2.06-2.24 (m, 2H), 2.41-2.67 (m, 2H), 3.61-3.74 (m, 1H), 4.56 (td, J=7.09, 3.64 Hz, 1H), 7.31-7.57 (m, 6H), 7.61-7.82 (m, 4H).

Preparation of (3S,5S)-5-[(1S)-1-[tert-butyl(diphenyl)silyl]oxypropyl]-3-[(1R)-1-hydroxyethyl]tetrahydrofuran-2-one (Compound 9f-A) and (3S,5S)-5-[(1S)-1-[tert-butyl(diphenyl)silyl]oxypropyl]-3-[(1S)-1-hydroxyethyl]tetrahydrofuran-2-one (Compound 9f-B)

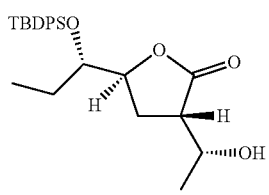

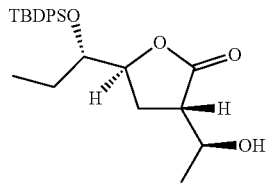

To a solution of (5S)-5-[(1S)-1-[tert-butyl(diphenyl)silyl]oxypropyl]tetrahydrofuran-2-one (200 g, 520 mmol) in THF (500 mL) was added LDA (390 mL, 780 mmol) slowly at −78° C. and stirred under N$_2$ for further 2 hours. To the above mixture was added CH$_3$CHO (34.4 g, 780 mmol) slowly at −78° C. and stirred for another 1 hour. The reaction was quenched with NH$_4$Cl (2 L), and diluted with EtOAc (2 L). The organic layer was washed with brine (1 L) and dried over anhydrous sodium sulfate, filtered, and the organic solvent was concentrated in vacuo to give the residue which was purified by column chromatography on silica gel (eluting with 0-10% EtOAc in petroleum ether) twice to give 42 g of (3S,5S)-5-[(1S)-1-[tert-butyl(diphenyl)silyl]oxypropyl]-3-[(1R)-1-hydroxyethyl]tetrahydrofuran-2-one (Compound 9f-A) and 46 g of (3S,5S)-5-[(1S)-1-[tert-butyl(diphenyl)silyl]oxypropyl]-3-[(1S)-1-hydroxyethyl]tetrahydrofuran-2-one (Compound 9f-B).

The stereochemistry on five member ring has been established by 2D NMR NOESY experiments. For Compound 9f-A and Compound 9f-B, correlation of C³H with C⁵H was not observed.

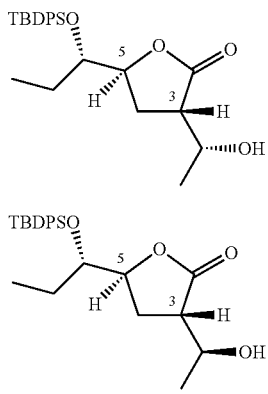

9f-A

9f-B

Compound 9f-A: [α]²⁵ +21.80 (c 1.03, MeOH); ¹H NMR (400 MHz, CDCl₃) δ ppm: 0.72 (t, J=7.53 Hz, 3H), 1.07 (s, 9H), 1.23 (d, J=6.40 Hz, 3H), 1.36-1.51 (m, 1H), 1.65-1.80 (m, 1H), 2.10-2.24 (m, 1H), 2.35 (dt, J=12.83, 9.08 Hz, 1H), 2.86 (ddd, J=10.29, 9.03, 3.14 Hz, 1H), 3.66 (ddd, J=8.28, 5.08, 2.95 Hz, 1H), 4.35 (dd, J=6.40, 3.01 Hz, 1H), 4.58 (dt, J=9.13, 3.15 Hz, 1H), 7.34-7.54 (m, 6H), 7.63-7.81 (m, 4H).

Compound 9f-B: [α]²⁵ +21.40 (c 0.97, MeOH); ¹H NMR (400 MHz, CDCl₃) δ ppm: 0.72 (t, J=7.47 Hz, 3H), 1.08 (s, 9H), 1.23 (d, J=6.27 Hz, 3H), 1.38-1.53 (m, 1H), 1.66-1.81 (m, 1H), 1.97 (dt, J=13.05, 9.60 Hz, 1H), 2.24 (ddd, J=12.92, 10.16, 2.51 Hz, 1H), 2.68-2.85 (m, 1H), 3.65 (ddd, J=8.34, 5.08, 2.89 Hz, 1H), 3.79-3.95 (m, 1H), 4.56 (dt, J=9.29, 2.64 Hz, 1H), 7.38-7.54 (m, 6H), 7.70 (ddd, J=10.57, 8.00, 1.51 Hz, 4H).

Preparation of [(1R)-1-[(3S,5S)-5-[(1S)-1-[tert-butyl(diphenyl)silyl]oxypropyl]-2-oxo-tetrahydrofuran-3-yl]ethyl] (2S)-3,3,3-trifluoro-2-methoxy-2-phenyl-propanoate (Compound 9g-A) and [(1R)-1-[(3S,5S)-5-[(1S)-1-[tert-butyl(diphenyl)silyl]oxypropyl]-2-oxo-tetrahydrofuran-3-yl]ethyl] (2R)-3,3,3-trifluoro-2-methoxy-2-phenyl-propanoate (Compound 9g-B)

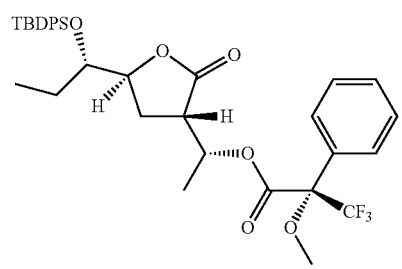

9g-A

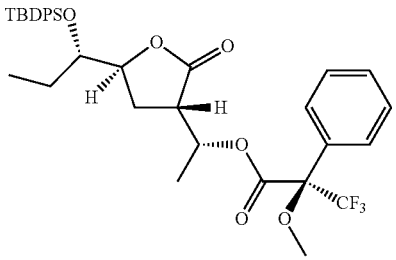

9g-B

To a solution of (3S,5S)-5-[(1S)-1-[tert-butyl(diphenyl)silyl]oxypropyl]-3-[(1R)-1-hydroxyethyl]tetrahydrofuran-2-one (Compound 9f-A) (20 mg, 0.047 mmol), DMAP (0.6 mg, 0.005 mmol) and Et₃N (9.5 mg, 0.094 mmol) in DCM (2 mL) was added (2R)-3,3,3-trifluoro-2-methoxy-2-phenyl-propanoyl chloride (24 mg, 0.094 mmol) slowly at 0° C. and stirred at 25-28° C. under N₂ for 12 hours. The reaction solution was quenched with water (3 mL), extracted with DCM (2 mL) twice and dried over Na₂SO₄. After concentrated in vacuo, the residue was purified by preparative TLC (eluting with 1:8 EtOAc in petroleum ether) to give [(1R)-1-[(3S,5S)-5-[(1S)-1-[tert-butyl(diphenyl)silyl]oxypropyl]-2-oxo-tetrahydrofuran-3-yl]ethyl] (2S)-3,3,3-trifluoro-2-methoxy-2-phenyl-propanoate (Compound 9g-A).

In analogy to Compound 9g-A, [(1R)-1-[(3S,5S)-5-[(1S)-1-[tert-butyl(diphenyl)silyl]oxypropyl]-2-oxo-tetrahydrofuran-3-yl]ethyl] (2R)-3,3,3-trifluoro-2-methoxy-2-phenyl-propanoate (Compound 9g-B) was prepared by using (2S)-3,3,3-trifluoro-2-methoxy-2-phenyl-propanoyl chloride instead of (2R)-3,3,3-trifluoro-2-methoxy-2-phenyl-propanoyl chloride.

Compound 9g-A: ¹H NMR (400 MHz, CDCl₃) δ ppm: 0.68 (t, J=7.47 Hz, 3H), 1.05 (s, 9H), 1.33-1.41 (m, 1H), 1.43 (d, J=6.40 Hz, 3H), 1.63-1.75 (m, 1H), 2.15-2.24 (m, 2H), 2.97 (td, J=9.63, 3.83 Hz, 1H), 3.50-3.55 (m, 3H), 3.58-3.64 (m, 1H), 4.37-4.45 (m, 1H), 5.54-5.63 (m, 1H), 7.37-7.48 (m, 9H), 7.48-7.54 (m, 2H), 7.63-7.72 (m, 4H).

Compound 9g-B: ¹H NMR (400 MHz, CDCl₃) δ ppm: 0.66 (t, J=7.40 Hz, 3H), 1.05 (s, 9H), 1.34 (d, J=6.27 Hz, 3H), 1.37-1.49 (m, 1H), 1.64-1.75 (m, 1H), 2.13-2.21 (m, 2H), 2.96 (td, J=9.41, 2.64 Hz, 1H), 3.51 (s, 3H), 3.57-3.64 (m, 1H), 4.38-4.49 (m, 1H), 5.50-5.61 (m, 1H), 7.36-7.51 (m, 11H), 7.68 (t, J=8.47 Hz, 4H).

According to the Mosher's model (*Chem. Rev.* 2004, 104, 17-117.) and ¹H NMR results, the absolute configurations of Compound 9g-A and Compound 9g-B are shown as above listed.

Preparation of [(3S,5S)-3-[(1R)-1-acetoxyethyl]-5-[(1S)-1-[tert-butyl(diphenyl)silyl]oxypropyl]tetrahydrofuran-2-yl] acetate (Compound 9h-A) and [(3S,5S)-3-[(1S)-1-acetoxyethyl]-5-[(1S)-1-[tert-butyl(diphenyl)silyl]oxypropyl]tetrahydrofuran-2-yl] acetate (Compound 9h-B)

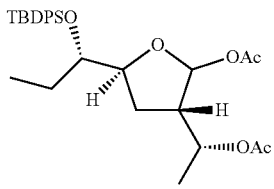

9h-A

-continued

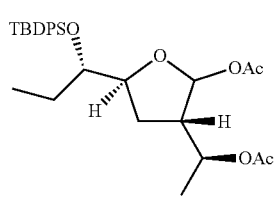

9h-B

To a solution of (3S,5S)-5-[(1S)-1-[tert-butyl(diphenyl)silyl]oxypropyl]-3-[(1R)-1-hydroxyethyl]tetrahydrofuran-2-one (Compound 9f-A) (17 g, 40 mmol) in toluene (200 mL) was added DIBAL-H (1M, 120 mL) dropwise at −78° C., and the mixture was stirred at −78° C. under N₂ for 1 hour. The reaction was quenched with saturated solution of NH₄Cl and extracted with EtOAc. The organic layer was separated and washed with brine, dried and concentrated to give the crude product, which was re-dissolved in pyridine (100 mL). To the above mixture was added DMAP (500 mg, 4 mmol) and Ac₂O (30 g, 300 mmol) at 0° C. After being stirred at 25° C. for 16 hours, the reaction was quenched with saturated solution of NaHCO₃ and extracted with EtOAc. The organic layer was separated and washed with brine, dried and concentrated to give the crude product, which was purified by silica gel column (eluting with 0-10% EtOAc in petroleum ether) to give 13 g of [(3S,5S)-3-[(1R)-1-acetoxyethyl]-5-[(1S)-1-[tert-butyl(diphenyl)silyl]oxypropyl]tetrahydrofuran-2-yl] acetate (Compound 9h-A) as a colorless oil.

In analogy to Compound 9h-A, [(3S,5S)-3-[(1S)-1-acetoxyethyl]-5-[(1S)-1-[tert-butyl(diphenyl)silyl]oxypropyl]tetrahydrofuran-2-yl] acetate (Compound 9h-B) was prepared by using (3S,5S)-5-[(1S)-1-[tert-butyl(diphenyl)silyl]oxypropyl]-3-[(1S)-1-hydroxyethyl]tetrahydrofuran-2-one (Compound 9f-B) instead of Compound 9f-A.

Preparation of [(1R)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl acetate (Compound 9i-A) and [(1S)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl]acetate (Compound 9i-B)

-continued

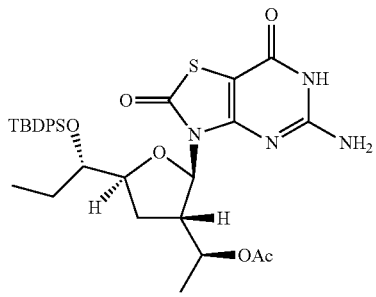

9i-B

To a suspension of 5-amino-3,6-dihydrothiazolo[4,5-d]pyrimidine-2,7-dione (3.6 g, 20 mmol) in MeCN (100 mL) was added BSA (16 g, 80 mmol) at 25° C., and the mixture was heated to 85° C. for 1 hour until a clear solution was formed. After the mixture was cooled to 0° C., [(3S,5S)-3-[(1R)-1-acetoxyethyl]-5-[(1S)-1-[tert-butyl(diphenyl)silyl]oxypropyl]tetrahydrofuran-2-yl] acetate (Compound 9h-A, 5.2 g, 10 mmol) was added, followed by addition of TMSOTf (4.4 g, 20 mmol). After being stirred at 25° C. for 16 hours, the reaction was quenched with saturated solution of NaHCO₃ and extracted with EtOAc. The organic layer was separated and washed with brine, dried and concentrated in vacuo to give the crude product, which was purified by silica gel column (eluting with 0-2% methanol in DCM) to give 6 g of [(1R)-1-[(2R,3S,5S)-2-(5-amino-2,7-dioxo-6H-thiazolo[4,5-d]pyrimidin-3-yl)-5-[(1 S)-1-[tert-butyl(diphenyl)silyl]oxypropyl]tetrahydrofuran-3-yl]ethyl] acetate (Compound 9i-A) as a yellow foam.

In analogy to Compound 9i-A, [(1S)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl]acetate (Compound 9i-B) was prepared by using [(3S,5S)-3-[(1S)-1-acetoxyethyl]-5-[(1S)-1-[tert-butyl(diphenyl)silyl]oxypropyl]tetrahydrofuran-2-yl] acetate (Compound 9h-B) instead of Compound 9h-A.

Preparation of [(1R)-1-[(2R,3S,5S)-2-(5-amino-2,7-dioxo-6H-thiazolo[4,5-d]pyrimidin-3-yl)-5-[(1S)-1-hydroxypropyl]tetrahydrofuran-3-yl]ethyl] acetate (Example 9-A) and [(1S)-1-[(2R,3S,5S)-2-(5-amino-2,7-dioxo-6H-thiazolo[4,5-d]pyrimidin-3-yl)-5-[(1S)-1-hydroxypropyl]tetrahydrofuran-3-yl]ethyl] acetate (Example 9-B)

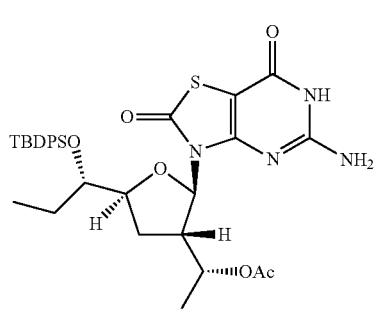

9i-A

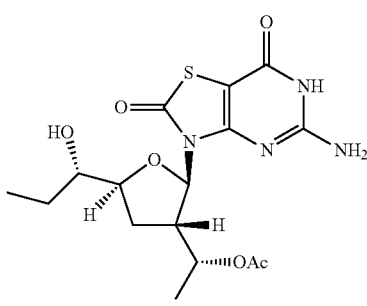

9-A

-continued

9-B

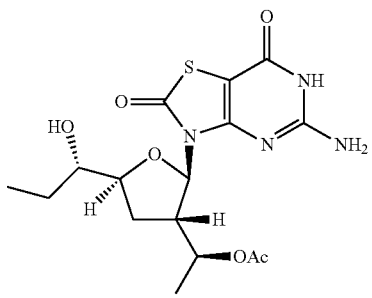

To a solution of [(1R)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl] acetate (Compound 9i-A, 5 g, 8 mmol) in MeOH (100 mL) was added NH$_4$F (7 g, 189 mmol) at 25° C., and the mixture was stirred at 90° C. for 5 days. The mixture was concentrated in vacuo to give the residue, which was purified by silica gel column (eluting with 0-3% methanol in DCM) to give 2 g of [(1R)-1-[(2R,3S,5S)-2-(5-amino-2,7-dioxo-6H-thiazolo[4,5-d]pyrimidin-3-yl)-5-[(1S)-1-hydroxypropyl]tetrahydrofuran-3-yl]ethyl] acetate (Example 9-A) as a yellow foam. The further purification by SFC gives Example 9-A as a white solid.

In analogy to Example 9-A, [(1S)-1-[(2R,3S,5S)-2-(5-amino-2,7-dioxo-6H-thiazolo[4,5-d]pyrimidin-3-yl)-5-[(1S)-1-hydroxypropyl]tetrahydrofuran-3-yl]ethyl] acetate (Example 9-B) was prepared by using [(1S)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl] acetate (Compound 9i-B) instead of Compound 9i-A.

Example 9-A: [α]$^{25}$ −10.80 (c 0.44, MeOH); MS obsd. (ESI$^+$) [(M+H)$^+$]: 399.2; $^1$H NMR (400 MHz, Methanol-d$_4$) δ ppm: 0.99 (t, J=7.6 Hz, 3H), 1.25 (d, J=6.4 Hz, 3H), 1.55-1.45 (m, 2H), 2.08-2.05 (m, 1H), 2.03 (s, 3H), 2.33-2.31 (m, 1H), 3.32-3.22 (m, 1H), 3.49-3.47 (m, 1H), 4.07-4.05 (m, 1H), 5.02-4.96 (m, 1H), 6.03 (d, J=6.4 Hz, 1H).

Example 9-B: [α]$^{25}$ +20.10 (c 0.51, MeOH); MS obsd. (ESI$^+$) [(M+H)$^+$]: 399.1; $^1$H NMR (400 MHz, Methanol-d$_4$) δ ppm: 0.97 (t, J=7.2 Hz, 3H), 1.25 (d, J=6.0 Hz, 3H), 1.54-1.48 (m, 2H), 1.82 (s, 3H), 1.94-1.84 (m, 1H), 2.35-2.32 (m, 1H), 3.22-3.18 (m, 1H), 3.47-3.44 (m, 1H), 4.10-4.05 (m, 1H), 5.04-4.93 (m, 1H), 6.01 (d, J=7.2 Hz, 1H).

Example 10

5-Amino-3-[(2R,3S,5S)-3-[(1R)-1-hydroxyethyl]-5-[(1S)-1-hydroxypropyl]tetrahydrofuran-2-yl]-6H-thiazolo[4,5-d]pyrimidine-2,7-dione (Example 10-A) and 5-amino-3-[(2R,3S,5S)-3-[(1S)-1-hydroxyethyl]-5-[(1S)-1-hydroxypropyl]tetrahydrofuran-2-yl]-6H-thiazolo[4,5-d]pyrimidine-2,7-dione (Example 10-B)

10-A

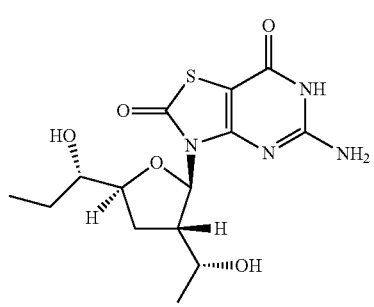

-continued

10-B

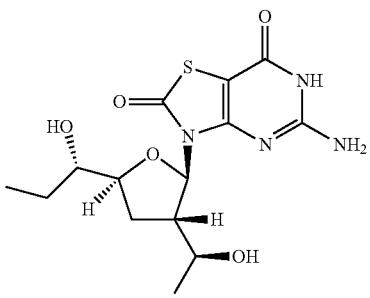

To a solution of [(1R)-1-[(2R,3S,5S)-2-(5-amino-2,7-dioxo-6H-thiazolo[4,5-d]pyrimidin-3-yl)-5-[(1S)-1-hydroxypropyl]tetrahydrofuran-3-yl]ethyl] acetate (Example 9-A, 1.5 g, 4 mmol) in MeOH (50 mL) was added K$_2$CO$_3$ (1.1 g, 8 mmol) at 25° C., and the mixture was stirred at 25° C. for 16 hours. The mixture was concentrated in vacuo and purified by preparative HPLC and SFC to give 117.4 mg of 5-amino-3-[(2R,3S,5S)-3-[(1R)-1-hydroxyethyl]-5-[(1S)-1-hydroxypropyl]tetrahydrofuran-2-yl]-6H-thiazolo[4,5-d]pyrimidine-2,7-dione (Example 10-A) as a white solid.

In analogy to Example 10-A, 5-amino-3-[(2R,3S,5S)-3-[(1S)-1-hydroxyethyl]-5-[(1S)-1-hydroxypropyl]tetrahydrofuran-2-yl]-6H-thiazolo[4,5-d]pyrimidine-2,7-dione (Example 10-B) was prepared by using [(1S)-1-[(2R,3S,5S)-2-(5-amino-2,7-dioxo-6H-thiazolo[4,5-d]pyrimidin-3-yl)-5-[(1S)-1-hydroxypropyl]tetrahydrofuran-3-yl]ethyl] acetate (Example 9-B) instead of Example 9-A.

Example 10-A: [α]$^{25}$ −17.8° (c 0.57, MeOH); MS obsd. (ESI$^+$) [(M+H)$^+$]: 357.1; $^1$H NMR (400 MHz, Methanol-d$_4$) δ ppm: 0.98 (t, J=7.2 Hz, 3H), 1.18 (d, J=6.4 Hz, 3H), 1.53-1.45 (m, 2H), 1.92-1.88 (m, 1H), 2.35-2.31 (m, 1H), 2.99-2.95 (m, 1H), 3.47-3.45 (m, 1H), 3.78 (t, J=6.8 Hz, 1H), 4.05-4.02 (m, 1H), 6.19 (d, J=6.4 Hz, 1H).

Example 10-B: [α]$^{25}$ +7.1° (c 0.61, MeOH); MS obsd. (ESI$^+$) [(M+H)$^+$]: 357.0; $^1$H NMR (400 MHz, Methanol-d$_4$) δ ppm: 1.00 (t, J=7.40 Hz, 3H), 1.20 (d, J=6.27 Hz, 3H) 1.40-1.64 (m, 2H), 1.92 (ddd, J=12.55, 7.72, 6.21 Hz, 1H) 2.35 (ddd, J=12.42, 9.79, 6.90 Hz, 1H), 2.99 (dq, J=9.80, 6.39 Hz, 1H) 3.47 (dt, J=8.69, 4.38 Hz, 1H), 3.80 (quin, J=6.46 Hz, 1H), 4.06 (td, J=7.34, 4.64 Hz, 1H), 6.17-6.24 (m, 1H).

Example 11

[(1R)-1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]ethyl] ethyl carbonate

11

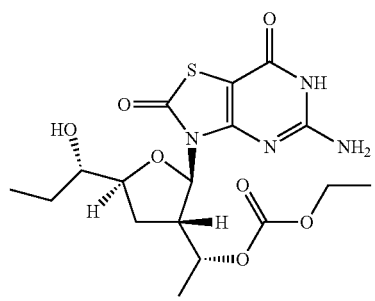

Preparation of [(1R)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] acetate

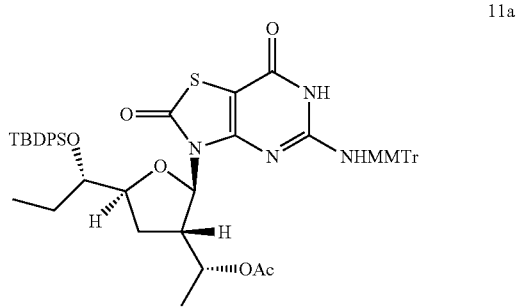

11a

To a solution of [(1R)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl] acetate (Compound 9i-A, 3.7 g, 5.8 mmol) in DCM (100 mL) was added Collidine (2.1 g, 17.4 mmol), AgNO$_3$ (2.9 g, 17.4 mmol) and MMTrCl (5.4 g, 17.4 mmol) at 0° C., and it was stirred at 20° C. for 2 hours. The reaction solution was quenched with water (80 mL), filtered, and extracted with EtOAc (100 mL) three times. The combined organic layer was dried over anhydrous sodium sulfate, filtered, concentrated, and the residue was purified by silica column (eluting with 1-5% methanol in DCM) to give 5 g of [(1R)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] acetate as a yellow solid. MS obsd. (ESI$^+$) [(M+H)$^+$]: 909.3.

Preparation of 3-[(2R,3S,5S)-5-[(1S)-1-[tert-butyl(diphenyl)silyl]oxypropyl]-3-[(1R)-1-hydroxyethyl]tetrahydrofuran-2-yl]-5-[[(4-methoxyphenyl)-diphenyl-methyl]amino]-6H-thiazolo[4,5-d]pyrimidine-2,7-dione

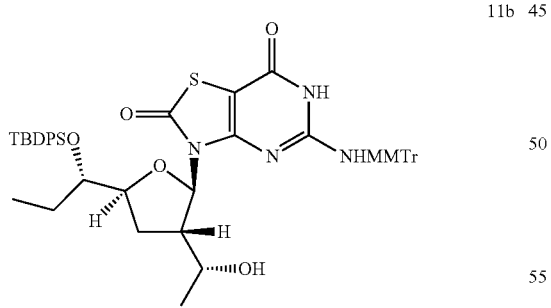

11b

To a solution of [(1R)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] acetate (5.0 g, 5.5 mmol) in methanol (60.0 mL) was added K$_2$CO$_3$ (4.5 g, 33.0 mmol). The mixture was stirred at 25° C. for 12 hours. The solid was removed by filtration, and the filtrate was concentrated in vacuo. The residue was purified by silica column (eluting with 2-5% methanol in DCM) to give 3.8 g of 3-[(2R,3S,5S)-5-[(1S)-1-[tert-butyl(diphenyl)silyl]oxypropyl]-3-[(1R)-1-hydroxyethyl]tetrahydrofuran-2-yl]-5-[[(4-methoxyphenyl)-diphenyl-methyl]amino]-6H-thiazolo[4,5-d]pyrimidine-2,7-dione as a white solid.

Preparation of [(1R)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl]ethyl carbonate

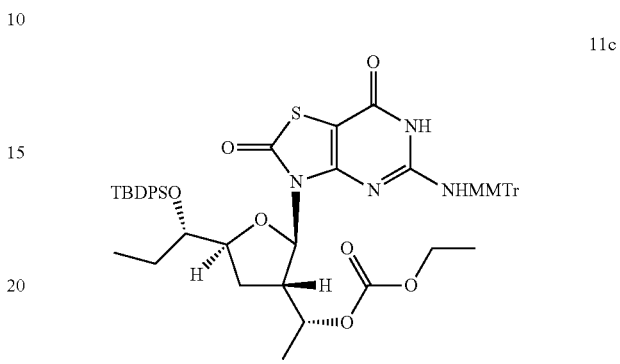

11c

To a solution of 3-[(2R,3S,5S)-5-[(1S)-1-[tert-butyl(diphenyl)silyl]oxypropyl]-3-[(1R)-1-hydroxyethyl]tetrahydrofuran-2-yl]-5-[[(4-methoxyphenyl)-diphenyl-methyl]amino]-6H-thiazolo[4,5-d]pyrimidine-2,7-dione (1.0 g, 1.15 mmol) and DMAP (140.3 mg, 1.15 mmol) in pyridine (10.0 mL) was added ethyl chloroformate (3.73 g, 34.6 mmol) at 25° C. The mixture was stirred at 110° C. for 12 hours. The mixture was poured into Na$_2$CO$_3$ solution (50.0 mL) and extracted with EtOAc (50.0 mL) three times. The combined organic layer was dried over Na$_2$SO$_4$. After filtration, the filtrate was concentrated in vacuo. The residue was purified by column chromatography on silica gel (eluting with 0.5-1% methanol in DCM) to give 0.6 g of [(1R)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] ethyl carbonate as a colorless foam. MS obsd. (ESI$^+$) [(M+H)$^+$]: 940.4.

Preparation of ethyl [(1R)-1-[(2R,3S,5S)-5-[(1S)-1-hydroxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] carbonate

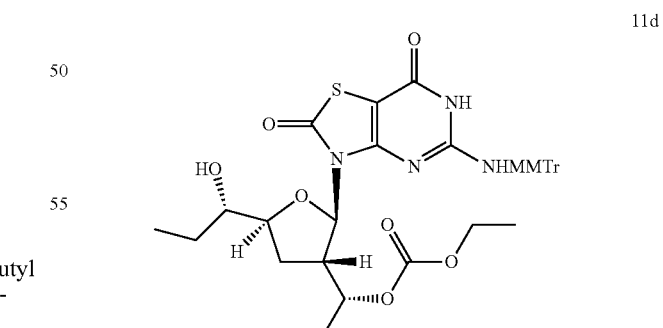

11d

A solution of [(1R)-1-[(2R,3S,5S)-5-[(1S)-1-[tert-butyl(diphenyl)silyl]oxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl]ethyl carbonate (600.0 mg, 0.64 mmol) in TBAF/THF (3 M, 10.0 mL) was stirred at 50° C. under N$_2$ for 16 hours. The mixture was diluted with water (100.0 mL) and extracted with EtOAc (50.0 mL) three times. The organic layer was washed with brine (50.0 mL) and dried over Na₂SO₄. After filtration, the filtrate was concentrated in vacuo. The crude product was purified by column chromatography on silica gel (eluting with 0.5-1% methanol in DCM) to give 350 mg of ethyl [(1R)-1-[(2R,3S,5S)-5-[(1S)-1-hydroxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl] carbonate as a colorless foam. MS obsd. (ESI⁺) [(M+H)⁺]: 701.2.

Preparation of [(1R)-1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]ethyl]ethyl carbonate

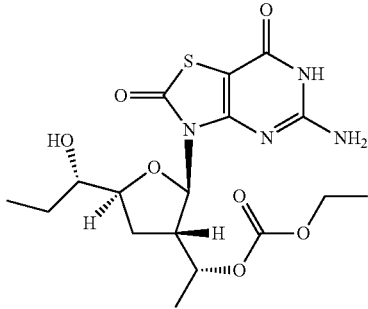

11

A solution of [(1R)-1-[(2R,3S,5S)-5-[(1S)-1-hydroxypropyl]-2-[5-[[(4-methoxyphenyl)-diphenyl-methyl]amino]-2,7-dioxo-6H-thiazolo[4,5-d]pyrimidin-3-yl]tetrahydrofuran-3-yl]ethyl]carbonate (330.0 mg, 0.47 mmol) in HCO₂H (10.0 mL) was stirred at 20-25° C. under N₂ for 0.5 hour. The mixture was concentrated in vacuo and purified by preparative HPLC and SFC to give 72 mg of [(1R)-1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]ethyl]ethyl carbonate as a white solid.

Example 11: MS obsd. (ESI⁺) [(M+H)⁺]: 429.2; ¹H NMR (400 MHz, Methanol-d₄) δ ppm: 1.00 (t, J=7.47 Hz, 3H), 1.26-1.33 (m, 6H), 1.39-1.64 (m, 2H), 2.04-2.16 (m, 1H), 2.36 (ddd, J=12.55, 9.72, 6.84 Hz, 1H), 3.24-3.30 (m, 1H), 3.49 (dt, J=8.60, 4.36 Hz, 1H), 4.02-4.12 (m, 1H), 4.17 (q, J=7.07 Hz, 2H), 4.82-4.87 (m, 1H), 6.06 (d, J=6.53 Hz, 1H).

Example 12

[(1R)-1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]ethyl] benzoate

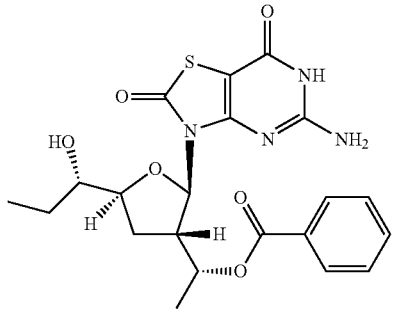

12

The title compound was prepared in analogy to Example 11, by using benzoyl chloride instead of ethyl chloroformate. The final product was purified by preparative HPLC and SFC to afford Example 12 as a white solid.

Example 12: MS obsd. (ESI⁺) [(M+H)⁺]: 461.0; ¹H NMR (400 MHz, Methanol-d₄) δ ppm: 1.01 (t, J=7.47 Hz, 3H), 1.43 (d, J=6.40 Hz, 3H), 1.46-1.54 (m, 2H), 1.54-1.64 (m, 1H), 2.10-2.24 (m, 2H), 2.37-2.50 (m, 1H), 3.43-3.50 (m, 1H), 3.53 (dt, J=8.82, 4.31 Hz, 1H), 4.10-4.20 (m, 1H), 5.27-5.37 (m, 1H), 6.23 (d, J=6.53 Hz, 1H), 7.41-7.52 (m, 2H), 7.56-7.69 (m, 1H), 7.95 (d, J=7.15 Hz, 2H).

Example 13

5-Amino-3-[(2R,3S,5S)-5-[(1S)-1-hydroxypropyl]-3-[(1R)-1-methoxyethyl]tetrahydrofuran-2-yl]-6H-thiazolo[4,5-d]pyrimidine-2,7-dione

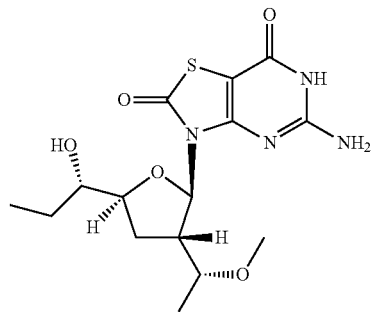

13

The title compound was prepared in analogy to Example 11, by using iodomethane instead of ethyl chloroformate. The final product was purified by preparative HPLC and SFC to afford Example 13 as a white foam.

Example 13: MS obsd. (ESI⁺) [(M+H)⁺]: 371.0; ¹H NMR (400 MHz, Methanol-d₄) δ ppm: 1.00 (t, J=7.40 Hz, 3H), 1.17 (d, J=6.15 Hz, 3H), 1.39-1.65 (m, 2H), 2.06-2.17 (m, 1H), 2.21-2.33 (m, 1H), 2.99-3.12 (m, 1H), 3.35 (s, 3H), 3.36-3.42 (m, 1H), 3.47 (dt, J=8.50, 4.47 Hz, 1H), 3.99-4.11 (m, 1H), 6.11 (d, J=6.52 Hz, 1H).

Example 14

5-Amino-3-[(2R,3S,5S)-3-[(1R)-1-benzyloxyethyl]-5-[(1S)-1-hydroxypropyl]tetrahydrofuran-2-yl]-6H-thiazolo[4,5-d]pyrimidine-2,7-dione

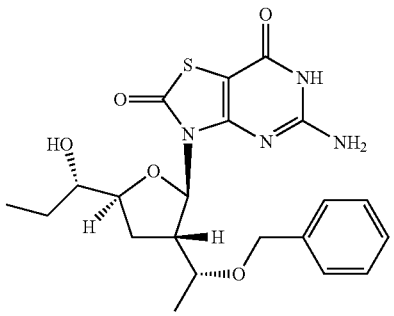

14

The title compound was prepared in analogy to Example 11, by using benzyl bromide instead of ethyl chloroformate.

The final product was purified by preparative HPLC to afford Example 14 as a white solid.

Example 14: MS obsd. (ESI+) [(M+H)+]: 447.0; 1H NMR (400 MHz, Methanol-d4) δ ppm: 0.99 (t, J=7.40 Hz, 3H), 1.25 (d, J=6.15 Hz, 3H), 1.37-1.63 (m, 2H), 2.06-2.19 (m, 1H), 2.29 (ddd, J=12.49, 9.85, 7.03 Hz, 1H), 3.11-3.24 (m, 1H), 3.48 (dt, J=8.78, 4.39 Hz, 1H), 3.64-3.74 (m, 1H), 4.04 (td, J=7.34, 4.77 Hz, 1H), 4.45 (d, J=11.54 Hz, 1H), 4.64 (d, J=11.54 Hz, 1H), 6.19 (d, J=6.27 Hz, 1H), 7.19-7.40 (m, 5H).

Example 15

3-[(2R,3S,5S)-3-[(1R)-1-Allyloxyethyl]-5-[(1S)-1-hydroxypropyl]tetrahydrofuran-2-yl]-5-amino-6H-thiazolo[4,5-d]pyrimidine-2,7-dione

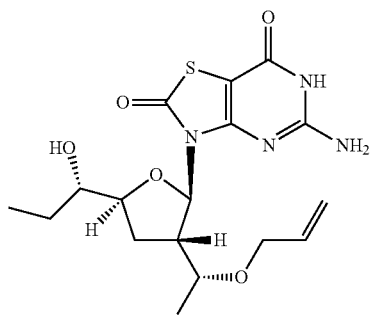

15

The title compound was prepared in analogy to Example 11, by using 3-bromoprop-1-ene instead of ethyl chloroformate. The final product was purified by preparative HPLC and SFC to afford Example 15 as a white solid.

Example 15: MS obsd. (ESI+) [(M+H)+]: 397.1; 1H NMR (400 MHz, Methanol-d4) δ ppm: 1.00 (t, J=7.47 Hz, 3H), 1.18 (d, J=6.27 Hz, 3H), 1.39-1.64 (m, 2H), 2.08-2.20 (m, 1H), 2.28 (ddd, J=12.39, 9.82, 7.03 Hz, 1H), 3.05-3.19 (m, 1H), 3.49 (dt, J=8.75, 4.34 Hz, 1H), 3.55-3.64 (m, 1H), 3.87-3.99 (m, 1H), 4.02-4.18 (m, 2H), 5.13 (dd, J=10.35, 1.69 Hz, 1H), 5.22-5.31 (m, 1H), 5.87-6.03 (m, 1H), 6.14 (d, J=6.40 Hz, 1H).

Example 16

5-Amino-3-[(2R,3S,5S)-5-[(1S)-1-hydroxypropyl]-3-[(1S)-1-methoxyethyl]tetrahydrofuran-2-yl]-6H-thiazolo[4,5-d]pyrimidine-2,7-dione

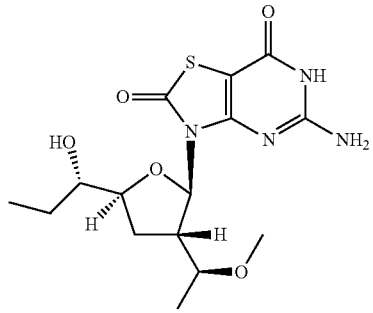

16

The title compound was prepared in analogy to Example 11 by using [(1S)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl] acetate (Compound 9i-B) instead of Compound 9i-A and iodomethane instead of ethyl chloroformate. The final product was purified by preparative HPLC to afford Example 16 as a white solid.

Example 16: MS obsd. (ESI+) [(M+H)+]: 371.1; 1H NMR (400 MHz, Methanol-d4) δ ppm: 1.00 (t, J=7.47 Hz, 3H), 1.17 (d, J=6.15 Hz, 3H), 1.40-1.62 (m, 2H), 1.91 (dt, J=12.45, 7.70 Hz, 1H), 2.31 (ddd, J=12.39, 9.69, 6.15 Hz, 1H), 2.92-3.07 (m, 1H), 3.27 (s, 3H), 3.36-3.42 (m, 1H), 3.46 (dt, J=8.50, 4.34 Hz, 1H), 4.07 (ddd, J=8.06, 6.18, 4.08 Hz, 1H), 6.13 (d, J=6.78 Hz, 1H).

Example 17

[(1S)-1-[(2S,4S,5R)-5-(5-Amino-2,7-dioxo-6H-thiazolo[4,5-d]pyrimidin-3-yl)-4-[(1R)-1-hydroxyethyl]tetrahydrofuran-2-yl]propyl] acetate

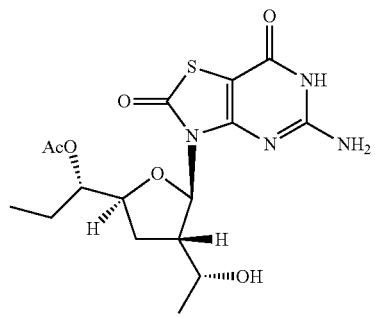

17

Preparation of 5-amino-3-[(2R,3S,5S)-5-[(1S)-1-[tert-butyl(diphenyl)silyl]oxypropyl]-3-[(1R)-1-hydroxyethyl]tetrahydrofuran-2-yl]-6H-thiazolo[4,5-d]pyrimidine-2,7-dione

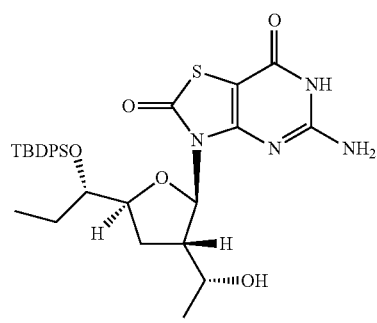

17a

To a solution of [(1R)-1-[(2R,3S,5S)-2-(5-amino-2,7-dioxo-6H-thiazolo[4,5-d]pyrimidin-3-yl)-5-[(1S)-1-[tert-butyl(diphenyl)silyl]oxypropyl]tetrahydrofuran-3-yl]ethyl] acetate (Compound 9i-A, 3.9 g, 6.1 mmol) in MeOH (50 mL) was added K2CO3 (3.4 g, 24.6 mmol) and the reaction mixture was stirred at 20° C. for 4 hours. The reaction was quenched with bubbling of CO2, and the solvent was removed by evaporation. The residue was re-dissolved in water (60 mL), extracted with EtOAc (50 mL) three times. The combined organic layer was dried over anhydrous sodium sulfate, filtered, concentrated, and the residue was used for the next step without further purification.

Preparation of 3-[(2R,3S,5S)-5-[(1S)-1-[tert-butyl (diphenyl)silyl]oxypropyl]-3-[(1R)-1-[(4-methoxyphenyl)-diphenyl-methoxy]ethyl]tetrahydrofuran-2-yl]-5-[[(4-methoxyphenyl)-diphenyl-methyl]amino]-6H-thiazolo[4,5-d]pyrimidine-2,7-dione

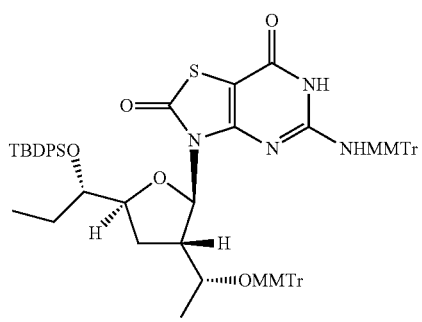

17b

To a solution of 5-amino-3-[(2R,3S,5S)-5-[(1S)-1-[tert-butyl(diphenyl)silyl]oxypropyl]-3-[(1R)-1-hydroxyethyl] tetrahydrofuran-2-yl]-6H-thiazolo[4,5-d]pyrimidine-2,7-dione (3.6 g, 6.1 mmol) in DCM (75 mL) was added Collidine (8.0 g, 66 mmol), AgNO$_3$ (4.4 g, 26 mmol) and MMTrCl (8.0 g, 26 mmol) at 0° C., and then the reaction mixture was stirred at 20° C. for 2 hours. The reaction solution was quenched with water (80 mL), filtered, and extracted with EtOAc (40 mL) three times. The combined organic layer was dried over anhydrous sodium sulfate, filtered, concentrated, and the residue was purified by silica column (eluting with 2-10% EtOAc in petroleum ether then 2% methanol in DCM) to give 5.1 g of 3-[(2R,3S,5S)-5-[(1S)-1-[tert-butyl (diphenyl)silyl]oxypropyl]-3-[(1R)-1-[(4-methoxyphenyl)-diphenyl-methoxy]ethyl]tetrahydrofuran-2-yl]-5-[[(4-methoxyphenyl)-diphenyl-methyl]amino]-6H-thiazolo[4,5-d]pyrimidine-2,7-dione as a yellow solid.

Preparation of 3-[(2R,3S,5S)-5-[(1S)-1-hydroxypropyl]-3-[(1R)-1-[(4-methoxyphenyl)-diphenyl-methoxy]ethyl]tetrahydrofuran-2-yl]-5-[[(4-methoxyphenyl)-diphenyl-methyl]amino]-6H-thiazolo[4,5-d]pyrimidine-2,7-dione

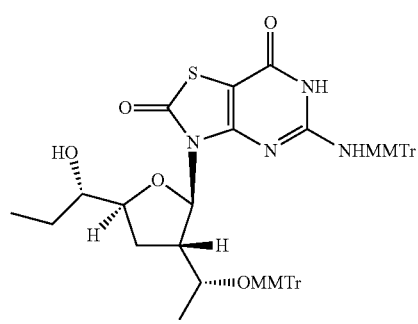

17c

A solution of 3-[(2R,3S,5S)-5-[(1S)-1-[tert-butyl(diphenyl)silyl]oxypropyl]-3-[(1R)-1-[(4-methoxyphenyl)-diphenyl-methoxy]ethyl]tetrahydrofuran-2-yl]-5-[[(4-methoxyphenyl)-diphenyl-methyl]amino]-6H-thiazolo[4,5-d] pyrimidine-2,7-dione (5.1 g, 4.5 mmol) in TBAF/THF (1M, 75 mL) was stirred at 50° C. for 72 hours. The reaction solution was diluted with water (200 mL), and then extracted with EtOAc (100 mL) three times. The combined organic layer was dried over anhydrous sodium sulfate, filtered, concentrated, and the residue was purified by silica column (eluting with 10-30% EtOAc in petroleum ether) to give 2 g of 3-[(2R,3S,5S)-5-[(1S)-1-hydroxypropyl]-3-[(1R)-1-[(4-methoxyphenyl)-diphenyl-methoxy]ethyl]tetrahydrofuran-2-yl]-5-[[(4-methoxyphenyl)-diphenyl-methyl]amino]-6H-thiazolo[4,5-d]pyrimidine-2,7-dione as a yellow solid.

Preparation of [(1S)-1-[(2S,4S,5R)-4-[(1R)-1-[(4-methoxyphenyl)-diphenyl-methoxy]ethyl]-5-[5-[[(4-methoxyphenyl)-diphenyl-methyl]amino]-2,7-dioxo-6H-thiazolo[4,5-d]pyrimidin-3-yl]tetrahydrofuran-2-yl]propyl] acetate

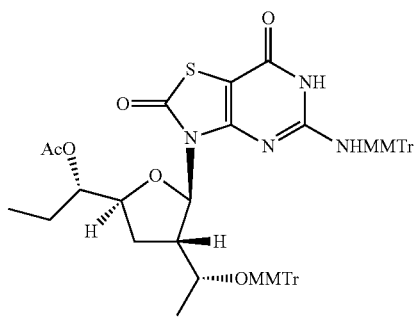

17d

To a solution of 3-[(2R,3S,5S)-5-[(1S)-1-hydroxypropyl]-3-[(1R)-1-[(4-methoxyphenyl)-diphenyl-methoxy]ethyl]tetrahydrofuran-2-yl]-5-[[(4-methoxyphenyl)-diphenyl-methyl]amino]-6H-thiazolo[4,5-d]pyrimidine-2,7-dione (1.9 g, 2.1 mmol) in pyridine (20 mL) was added DMAP (25.6 mg, 0.21 mmol) and acetyl chloride (494 mg, 6.3 mmol) at 0° C. and the reaction mixture was stirred at 20° C. for 3 hours. The reaction solution was diluted with EtOAc (60 mL), washed with aqueous NaHCO$_3$ (50 mL) and brine (10 mL). The organic layer was dried over anhydrous sodium sulfate, filtered, concentrated and the residue was purified by silica column (eluting with 20% EtOAc in petroleum ether and then 1% methanol in DCM) to give 1.5 g of [(1S)-1-[(2S,4S,5R)-4-[(1R)-1-[(4-methoxyphenyl)-diphenyl-methoxy]ethyl]-5-[5-[[(4-methoxyphenyl)-diphenyl-methyl]amino]-2,7-dioxo-6H-thiazolo[4,5-d]pyrimidin-3-yl]tetrahydrofuran-2-yl]propyl] acetate as a white solid.

Preparation of [(1S)-1-[(2S,4S,5R)-5-(5-amino-2,7-dioxo-6H-thiazolo[4,5-d]pyrimidin-3-yl)-4-[(1R)-1-hydroxyethyl]tetrahydrofuran-2-yl]propyl] acetate

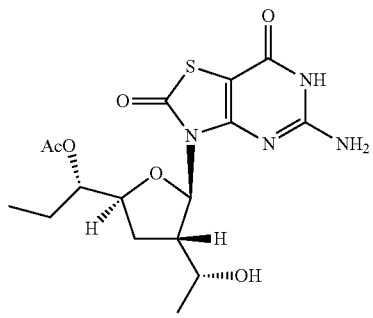

17

A solution of [(1S)-1-[(2S,4S,5R)-4-[(1R)-1-[(4-methoxyphenyl)-diphenyl-methoxy]ethyl]-5-[5-[[(4-methoxyphenyl)-diphenyl-methyl]amino]-2,7-dioxo-6H-thiazolo[4,5-d]pyrimidin-3-yl]tetrahydrofuran-2-yl]propyl] acetate (1.4 g, 1.48 mmol) in HCO₂H/H₂O (8 mL/2 mL) was stirred at 25° C. for 1 hour. The reaction solution was diluted with EtOAc (100 mL), neutralized with saturated aqueous NaHCO₃ (50 mL) and separated. The separated organic layer was dried over anhydrous sodium sulfate, filtered and concentrated to give the residue, which was purified by silica column (eluting with 20-50% EtOAc in petroleum ether), SFC and preparative HPLC to give 202.6 mg of [(1S)-1-[(2S,4S,5R)-5-(5-amino-2,7-dioxo-6H-thiazolo[4,5-d]pyrimidin-3-yl)-4-[(1R)-1-hydroxyethyl]tetrahydrofuran-2-yl]propyl] acetate as a white solid.

Example 17: MS obsd. (ESI⁺) [(M+H)⁺]: 399.0; ¹H NMR (400 MHz, Methanol-d₄) δ ppm: 0.92 (t, J=7.40 Hz, 3H), 1.20 (d, J=6.27 Hz, 3H), 1.52-1.65 (m, 1H), 1.66-1.79 (m, 1H), 2.01-2.12 (m, 1H), 2.04 (s, 3H), 2.35 (dt, J=12.33, 9.96 Hz, 1H), 2.99 (qd, J=6.30, 3.45 Hz, 1H), 3.86 (quin, J=6.12 Hz, 1H), 4.14 (dt, J=9.51, 6.85 Hz, 1H), 5.00 (ddd, J=8.56, 6.87, 3.76 Hz, 1H), 6.08 (d, J=4.14 Hz, 1H).

Example 18

5-Amino-3-[(2R,3S,5S)-3-[hydroxy(phenyl)methyl]-5-[(1S)-1-hydroxypropyl]tetrahydrofuran-2-yl]-6H-thiazolo[4,5-d]pyrimidine-2,7-dione

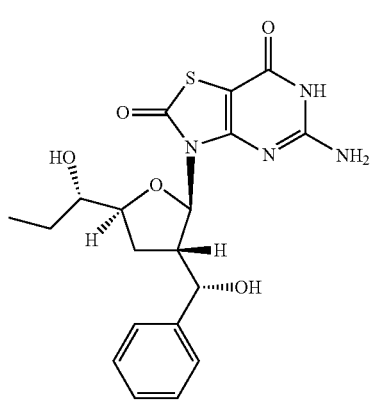

18

The title compound was prepared in analogy to Example 10, by using benzaldehyde instead of acetaldehyde. Example 18 was purified by preparative HPLC and SFC to afford Example 18-A and Example 18-B as white solid.

Example 18-A: MS obsd. (ESI⁺) [(M+H)⁺]: 491.1; ¹H NMR (400 MHz, Methanol-d₄) δ ppm: 0.99 (t, J=7.40 Hz, 3H), 1.39-1.63 (m, 2H), 2.26 (dt, J=12.86, 8.50 Hz, 1H), 2.43 (ddd, J=13.11, 8.85, 4.77 Hz, 1H), 3.47 (dt, J=8.50, 4.34 Hz, 1H), 3.63 (quin, J=8.47 Hz, 1H), 4.08 (dt, J=8.50, 4.47 Hz, 1H), 4.53 (d, J=8.41 Hz, 1H), 5.91 (d, J=7.91 Hz, 1H), 7.09-7.16 (m, 1H), 7.19 (t, J=7.22 Hz, 2H), 7.25-7.29 (m, 2H).

Example 18-B: MS obsd. (ESI⁺) [(M+H)⁺]: 491.1; ¹H NMR (400 MHz, Methanol-d₄) δ ppm: 0.98 (t, J=7.40 Hz, 3H), 1.38-1.60 (m, 2H), 2.01-2.11 (m, 1H), 2.12-2.26 (m, 1H), 3.43 (dt, J=8.56, 4.31 Hz, 1H), 3.49-3.61 (m, 1H), 3.97-4.12 (m, 1H), 4.77 (d, J=6.40 Hz, 1H), 6.24 (d, J=6.78 Hz, 1H), 7.14-7.20 (m, 1H), 7.25 (t, J=7.47 Hz, 2H), 7.34 (d, J=7.40 Hz, 2H).

Example 19

[1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]-1-methyl-ethyl] acetate

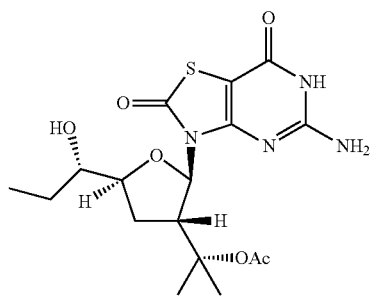

19

The title compound was prepared in analogy to Example 9, by using acetone instead of acetaldehyde. The final product was purified by SFC to afford Example 19 as a white solid.

Example 19: MS obsd. (ESI⁺) [(M+H)⁺]: 413.0; ¹H NMR (400 MHz, Methanol-d₄) δ ppm: 1.01 (t, J=7.40 Hz, 3H), 1.44-1.60 (m, 2H), 1.546 (s, 3H), 1.552 (s, 3H), 1.88 (s, 3H), 2.04 (ddd, J=12.83, 7.37, 5.90 Hz, 1H), 2.28-2.44 (m, 1H), 3.44-3.58 (m, 2H), 3.97-4.10 (m, 1H), 6.27 (d, J=6.15 Hz, 1H).

Example 20

5-Amino-3-[(2R,3S,5S)-3-(1-hydroxy-1-methyl-ethyl)-5-[(1S)-1-hydroxypropyl]tetrahydrofuran-2-yl]-6H-thiazolo[4,5-d]pyrimidine-2,7-dione

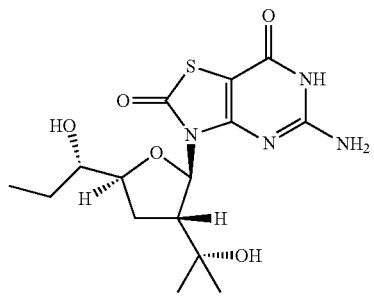

20

The title compound was prepared in analogy to Example 10, by using acetone instead of acetaldehyde. The final product was purified by SFC to afford Example 20 as a white solid.

Example 20: MS obsd. (ESI+) [(M+H)+]: 371.0; 1H NMR (400 MHz, Methanol-d4) δ ppm: 0.88 (t, J=7.28 Hz, 3H), 1.06 (s, 3H), 1.11 (s, 3H), 1.16-1.31 (m, 1H), 1.41 (m, 1H), 1.90 (m, 1H), 2.00-2.20 (m, 1H), 2.81-2.92 (m, 1H), 3.62-3.89 (m, 1H), 4.40 (d, J=5.65 Hz, 1H), 4.51 (s, 1H), 6.06 (d, J=5.02 Hz, 1H), 6.89 (br. s., 2H), 11.14 (br. s., 1H).

Example 21

[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl] acetate

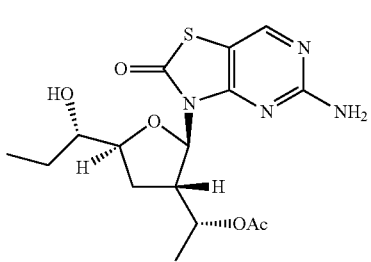

The title compound was prepared in analogy to Example 9, by using 5-amino-3H-thiazolo[4,5-d]pyrimidin-2-one (CAS: 848691-22-5, WuXi AppTec) instead of 5-amino-3,6-dihydrothiazolo[4,5-d]pyrimidine-2,7-dione. The final product was purified by SFC to afford Example 21 as a white solid.

Example 21: [α]$^{25}$ −11.00 (c 0.62, MeOH); MS obsd. (ESI+) [(M+H)+]: 383.1; 1H NMR (400 MHz, Methanol-d4) δ ppm: 1.01 (t, J=7.40 Hz, 3H), 1.27 (d, J=6.40 Hz, 3H), 1.41-1.68 (m, 2H), 2.04 (s, 3H), 2.07-2.20 (m, 1H), 2.39 (ddd, J=12.64, 9.57, 6.53 Hz, 1H), 3.24-3.31 (m, 1H), 3.52 (dt, J=8.72, 4.42 Hz, 1H), 4.12 (ddd, J=7.84, 6.59, 4.64 Hz, 1H), 4.97-5.08 (m, 1H), 6.14 (d, J=6.65 Hz, 1H), 8.25 (s, 1H).

Example 22

[(1S)-1-[(2S,4S,5R)-5-(5-Amino-2-oxo-thiazolo[4,5-d]pyrimidin-3-yl)-4-[(1R)-1-hydroxyethyl]tetrahydrofuran-2-yl]propyl] acetate

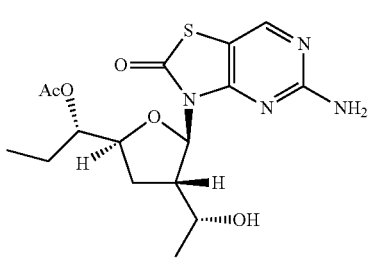

The title compound was prepared in analogy to Example 17, by using 5-amino-3H-thiazolo[4,5-d]pyrimidin-2-one instead of 5-amino-3,6-dihydrothiazolo[4,5-d]pyrimidine-2,7-dione. The final product was purified by SFC and preparative HPLC to afford Example 22 as a white solid.

Example 22: MS obsd. (ESI+) [(M+H)+]: 383.1; 1H NMR (400 MHz, Methanol-d4) δ ppm: 0.93 (t, J=7.40 Hz, 3H), 1.21 (d, J=6.27 Hz, 3H), 1.52-1.65 (m, 1H), 1.72 (dtd, J=14.51, 7.46, 7.46, 3.83 Hz, 1H), 2.02 (s, 3H), 2.09 (ddd, J=12.49, 6.96, 2.64 Hz, 1H), 2.39 (dt, J=12.33, 9.83 Hz, 1H), 2.99-3.10 (m, 1H), 3.89 (quin, J=6.09 Hz, 1H), 4.17 (dt, J=9.41, 6.90 Hz, 1H), 4.96-5.08 (m, 1H), 6.19 (d, J=3.89 Hz, 1H), 8.20 (s, 1H).

Example 23

[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl] 2-methylpropanoate

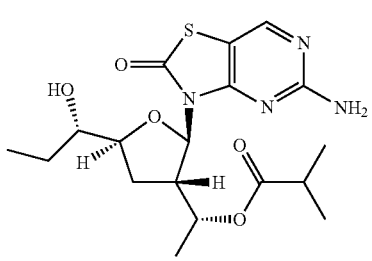

The title compound was prepared in analogy to Example 11, by using 5-amino-3H-thiazolo[4,5-d]pyrimidin-2-one instead of 5-amino-3,6-dihydrothiazolo[4,5-d]pyrimidine-2,7-dione and isobutyryl chloride instead of ethyl chloroformate. The final product was purified by SFC to afford Example 23 as a white solid.

Example 23: MS obsd. (ESI+) [(M+H)+]: 411.0; 1H NMR (400 MHz, Methanol-d4) δ ppm: 1.01 (t, J=7.47 Hz, 3H), 1.10-1.18 (m, 6H), 1.27 (d, J=6.40 Hz, 3H), 1.38-1.66 (m, 2H), 2.07-2.19 (m, 1H,) 2.41 (ddd, J=12.58, 9.69, 6.59 Hz, 1H), 2.52 (quin, J=6.96 Hz, 1H), 3.28-3.35 (m, 1H), 3.52 (dt, J=8.69, 4.38 Hz, 1H), 4.13 (ddd, J=7.78, 6.71, 4.58 Hz, 1H), 4.95-5.10 (m, 1H), 6.16 (d, J=6.65 Hz, 1H), 8.25 (s, 1H).

Example 24

[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl] 2,2-dimethylpropanoate

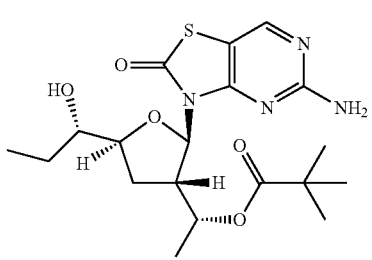

The title compound was prepared in analogy to Example 11, by using 5-amino-3H-thiazolo[4,5-d]pyrimidin-2-one instead of 5-amino-3,6-dihydrothiazolo[4,5-d]pyrimidine-2,7-dione, and by using pivaloyl chloride instead of ethyl chloroformate. The final product was purified by SFC to afford Example 24 as a white solid.

Example 24: MS obsd. (ESI+) [(M+H)+]: 425.0; 1H NMR (400 MHz, Methanol-d4) δ ppm: 1.01 (t, J=7.40 Hz, 3H), 1.17 (s, 9H), 1.27 (d, J=6.40 Hz, 3H), 1.42-1.68 (m, 2H), 2.05-2.19 (m, 1H), 2.42 (ddd, J=12.64, 9.76, 6.59 Hz, 1H), 3.30-3.37 (m, 1H), 3.53 (dt, J=8.63, 4.41 Hz, 1H), 4.07-4.22 (m, 1H), 4.94-5.07 (m, 1H), 6.17 (d, J=6.65 Hz, 1H), 8.25 (s, 1H).

Example 25

[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl] 3-methylbutanoate

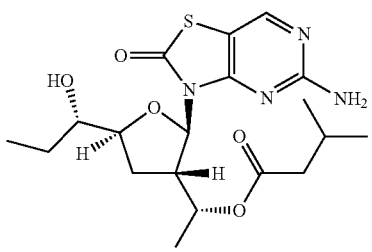

The title compound was prepared in analogy to Example 11, by using 5-amino-3H-thiazolo[4,5-d]pyrimidin-2-one instead of 5-amino-3,6-dihydrothiazolo[4,5-d]pyrimidine-2,7-dione, and by using 3-methylbutanoyl chloride instead of ethyl chloroformate. The final product was purified by SFC to afford Example 25 as a white solid.

Example 25: MS obsd. (ESI+) [(M+H)+]: 425.1; 1H NMR (400 MHz, Methanol-d4) δ ppm: 0.93 (d, J=6.65 Hz, 6H), 1.01 (t, J=7.47 Hz, 3H), 1.28 (d, J=6.40 Hz, 3H), 1.40-1.66 (m, 2H), 1.96-2.23 (m, 4H), 2.40 (ddd, J=12.64, 9.69, 6.78 Hz, 1H), 3.27-3.30 (m, 1H), 3.52 (dt, J=8.78, 4.39 Hz, 1H), 4.11 (td, J=7.31, 4.83 Hz, 1H), 5.01-5.13 (m, 1H), 6.17 (d, J=6.53 Hz, 1H), 8.25 (s, 1H).

Example 26

[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl] ethyl carbonate

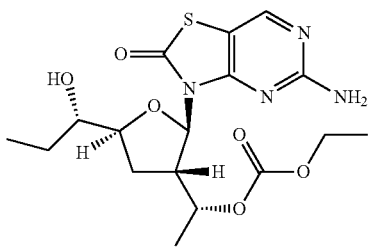

The title compound was prepared in analogy to Example 11, by using 5-amino-3H-thiazolo[4,5-d]pyrimidin-2-one instead of 5-amino-3,6-dihydrothiazolo[4,5-d]pyrimidine-2,7-dione. The final product was purified by SFC to afford Example 26 as a white solid.

Example 26: MS obsd. (ESI+) [(M+Na)+]: 435.1; 1H NMR (400 MHz, Methanol-d4) δ ppm: 1.01 (t, J=7.40 Hz, 3H), 1.28 (t, J=7.15 Hz, 3H), 1.31 (d, J=6.27 Hz, 3H), 1.40-1.67 (m, 2H), 2.04-2.20 (m, 1H), 2.39 (ddd, J=12.64, 9.63, 6.59 Hz, 1H), 3.29-3.36 (m, 1H), 3.51 (dt, J=8.78, 4.39 Hz, 1H), 4.09-4.14 (m, 1H), 4.17 (q, J=7.03 Hz, 2H), 4.84-4.89 (m, 1H), 6.15 (d, J=6.65 Hz, 1H), 8.25 (s, 1H).

Example 27

HEK293-Blue-hTLR-7 Cells Assay:

A stable HEK293-Blue-hTLR-7 cell line was purchased from InvivoGen (Cat.#: hkb-htlr7, San Diego, Calif., USA). These cells were designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was regulated by the NF-κB promoter upon stimulation of human TLR7. The cell culture supernatant SEAP reporter activity was determined using QUANTI-Blue™ kit (Cat.#: rep-qb1, Invivogen, San Diego, Ca, USA) at a wavelength of 640 nm, a detection medium that turns purple to blue in the presence of alkaline phosphatase.

HEK293-Blue-hTLR7 cells were incubated at a density of 250,000~450,000 cells/mL in a volume of 180 μL in a 96-well plate in Dulbecco's Modified Eagle's medium (DMEM) containing 4.5 g/l glucose, 50 U/ml penicillin, 50 mg/ml streptomycin, 100 mg/ml Normocin, 2 mM L-glutamine, 10% (v/v) heat-inactivated fetal bovine serum for 24 h. Then the HEK293-Blue-hTLR-7 cells were incubated with addition of 20 μL test compound in a serial dilution in the presence of final DMSO at 1% and perform incubation under 37° C. in a CO2 incubator for 20 hours. Then 20 μL of the supernatant from each well was incubated with 180 μL Quanti-blue substrate solution at 37° C. for 1-3 hours and the absorbance was read at 620~655 nm using a spectrophotometer. The signalling pathway that TLR7 activation leads to downstream NF-κB activation has been widely accepted, and therefore similar reporter assay was also widely used for evaluating TLR7 agonist (Tsuneyasu Kaisho and Takashi Tanaka, Trends in Immunology, Volume 29, Issue 7, July 2008, Pages 329.sci; Hiroaki Hemmi et al, Nature Immunology 3, 196-200 (2002).

The compounds of the present invention were tested in the above assay for their TLR7 agonism activity as described herein and results are listed in Table 1. The Examples were found to have EC50 of about 3 μM to about 500 μM. Particular compounds of formula (I) or (Ia) were found to have EC50 of about 3 μM to about 200 μM.

TABLE 1

| Activity of Compounds in HEK293-hTLR-7 assay | |
|---|---|
| Example No. | HEK293-hTLR-7 EC50 (μM) |
| 1-B | 39 |
| 2-A | 156 |
| 3-A | 111 |
| 4-A | 205 |
| 5-A | 111 |

TABLE 1-continued

Activity of Compounds in HEK293-hTLR-7 assay

| Example No. | HEK293-hTLR-7 $EC_{50}$ (μM) |
| --- | --- |
| 6-A | 79 |
| 7 | 225 |
| 8 | 23 |
| 9-A | 8.4 |
| 9-B | 9.3 |
| 10-A | 2.7 |
| 10-B | 35 |
| 11 | 26 |
| 12 | 6.5 |
| 13 | 36 |
| 14 | 60 |
| 15 | 68 |
| 16 | 35 |
| 17 | 15 |
| 18-A | 10.4 |
| 18-B | 9.7 |
| 19 | 19 |
| 20 | 3 |

Example 28

Metabolism of Prodrugs: Compounds of Formula (II)

A study was undertaken to evaluate the metabolic conversion of prodrugs, compounds of formula (II) or (IIa), to compounds of formula (I) or (Ia) of the present invention. The produgs, compounds of formula (II) or (IIa), can be metabolized to the active compound of formula (I) or (Ia) and other compounds of the invention in the body if they are served as prodrugs. Hepatocytes are often used to assess the degree of metabolic conversion of prodrugs in the body of animal or human.

A study was undertaken to evaluate the metabolic conversion of prodrug Example 21, Example 22, Example 23, Example 24, Example 25 and Example 26, to the corresponding active form, Example 10-A, in the presence of human hepatocytes. The formation of active form, Example 10-A, was monitored in the study. For comparison, the metabolic conversion of famciclovir to penciclovir was also assessed.

Hepatocytes Suspension

Cryopreserved hepatocytes plating medium (Cat.#: PY-HMD-03) was purchased from RILD Research Institute for Liver Diseases (Shanghai) Co. Ltd. Cryopreserved human hepatocyte (Cat.#: X008005, Lot#:VRR) was purchased from BioreclamationIVT (Baltimore, Md.).

The stock hepatocyte suspension was prepared from cryopreserved hepatocytes in plating medium at the concentration of $1.8 \times 10^6$ cells/mL.

Working Solutions of Compounds

Compounds were dissolved in DMSO to make 10 mM stock solutions. 10 μL of the stock solution was diluted to 990 μL plating medium to get a 100 μM working solution.

Incubations

Reaction suspensions were prepared in 24-well cell culture plate by mixing 200 μL of hepatocytes suspension (human) and 200 μL of working solution. The final incubation contained $0.9 \times 10^6$ cells/mL and 50 μM compound. The above mixtures were incubated at 37° C. in a humidified 5% $CO_2$ atmosphere, with a 900 rpm shaking.

Preparation of Samples for Analysis

After 180 min of incubation, 200 μL of the incubation mixture was transferred to 1.5 mL tube and quenched with 400 μL stop solution (ice-cold acetonitrile with 0.2 μM Tolbutamide as internal standard). The samples were centrifuged at 14000 rpm for 10 minutes and the resultant supernatants were subjected to LC-MS/MS analysis.

The calibration curves were prepared in the following way. To a 200 μL of cell suspension (cell density of 1.8 million cells/mL), 198 μL of hepatocyte plating medium and 2 μL of the appropriate concentration of the compound in DMSO were added. Samples were mixed thoroughly and 200 μL of the mixture was transferred to 400 μL of the stop solution (see above). The standard curve range is from 1 μM to 25 μM.

Bioanalysis

The compounds were quantified on an API5500 LC-MC/MC instrument in the ESI-Positive MRM mode. The results of prodrug conversion and metabolite generation are summarized in Table 2.

TABLE 2

Concentration of the metabolites formed in human hepatocytes after 3-hour incubation of 50 μM of prodrugs.

| Example No. | Metabolized Product | Product Concentration in human hepatocytes (μM) |
| --- | --- | --- |
| 21 | 10-A | 2.18 |
| 22 | 10-A | 1.62 |
| 23 | 10-A | 2.85 |
| 24 | 10-A | 1.42 |
| 25 | 10-A | 2.28 |
| 26 | 10-A | 2.04 |
| Famciclovir | Penciclovir | 18 |

In human hepatocytes, compound Example 21, Example 22, Example 23, Example 24, Example 25, Example 26 as well as famciclovir were metabolized to yield the corresponding active metabolites Example 10-A and penciclovir, respectively.

The invention claimed is:
1. A compound of formula (I),

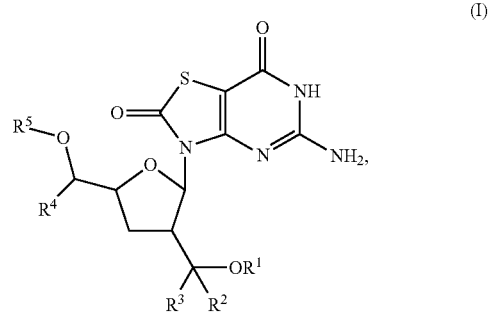

wherein
$R^1$ is H, $C_{1-6}$alkyl, $C_{2-6}$alkenyl, phenyl$C_{1-6}$alkyl, $C_{1-6}$alkylcarbonyl, $C_{1-6}$alkoxycarbonyl or phenylcarbonyl;
$R^2$ and $R^3$ are independently selected from H, $C_{1-6}$alkyl, $C_{3-7}$cycloalkyl, phenyl and pyridinyl, said phenyl and pyridinyl being unsubstituted or substituted with one to three substituents independently selected from $C_{1-6}$alkyl, halogen and $C_{1-6}$alkoxy;
$R^4$ is H or $C_{1-6}$alkyl; and
$R^5$ is H or $C_{1-6}$alkylcarbonyl;
or a pharmaceutically acceptable salt, enantiomer or diastereomer thereof.

2. A compound of formula (Ia) according to claim 1,

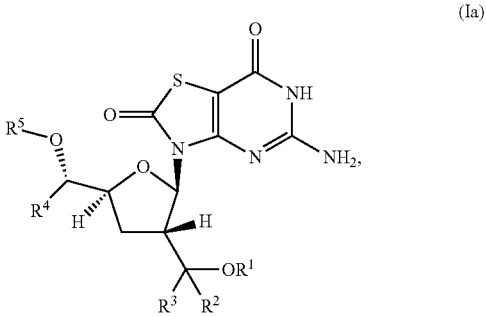

(Ia)

wherein
$R^1$ is H, $C_{1-6}$alkyl, $C_{2-6}$alkenyl, phenyl$C_{1-6}$alkyl, $C_{1-6}$alkylcarbonyl, $C_{1-6}$alkoxycarbonyl or phenylcarbonyl;
$R^2$ and $R^3$ are independently selected from H, $C_{1-6}$alkyl, $C_{3-7}$cycloalkyl, phenyl and pyridinyl, said phenyl and pyridinyl being unsubstituted or substituted with one to three substituents independently selected from $C_{1-6}$alkyl, halogen and $C_{1-6}$alkoxy;
$R^4$ is H or $C_{1-6}$alkyl; and
$R^5$ is H or $C_{1-6}$alkylcarbonyl;
or a pharmaceutically acceptable salt, enantiomer or diastereomer thereof.

3. A compound according to claim 1, wherein $R^1$ is H, $C_{1-6}$alkyl, $C_{1-6}$alkylcarbonyl, $C_{1-6}$alkoxycarbonyl or phenylcarbonyl; or a pharmaceutically acceptable salt, enantiomer or diastereomer thereof.

4. A compound according to claim 1, wherein $R^1$ is H, methyl, acetyl, ethoxycarbonyl or phenylcarbonyl; or a pharmaceutically acceptable salt, enantiomer or diastereomer thereof.

5. A compound according to claim 1, wherein $R^2$ and $R^3$ are independently selected from H, $C_{1-6}$alkyl and phenyl, said phenyl being unsubstituted or substituted with one to three substituents independently selected from $C_{1-6}$alkyl, halogen and $C_{1-6}$alkoxy; provided that $R^2$ and $R^3$ are not H simultaneously; or a pharmaceutically acceptable salt, enantiomer or diastereomer thereof.

6. A compound according to claim 1, wherein $R^2$ and $R^3$ are independently selected from H, methyl, ethyl, phenyl, chlorophenyl and methoxyphenyl; provided that $R^2$ and $R^3$ are not H simultaneously; or a pharmaceutically acceptable salt, enantiomer or diastereomer thereof.

7. A compound according to claim 1, wherein
$R^1$ is H;
$R^2$ and $R^3$ are independently selected from H, $C_{1-6}$alkyl and phenyl; provided that $R^2$ and $R^3$ are not H simultaneously;
$R^4$ is H or $C_{1-6}$alkyl; and
$R^5$ is H or $C_{1-6}$alkylcarbonyl;
or a pharmaceutically acceptable salt, enantiomer or diastereomer thereof.

8. A compound according to claim 1, wherein
$R^1$ is H;
$R^2$ and $R^3$ are independently selected from H, methyl and phenyl; provided that $R^2$ and $R^3$ are not H simultaneously;
$R^4$ is H or ethyl; and
$R^5$ is H or acetyl;
or a pharmaceutically acceptable salt, enantiomer or diastereomer thereof.

9. A compound according to claim 1 selected from:
5-Amino-3-[(2R,3S,5S)-3-(1-hydroxyethyl)-5-(hydroxymethyl)tetrahydrofuran-2-yl]-6H-thiazolo[4,5-d]pyrimidine-2,7-dione;
5-Amino-3-[(2R,3S,5S)-3-[cyclopropyl(hydroxy)methyl]-5-(hydroxymethyl)tetrahydrofuran-2-yl]-6H-thiazolo[4,5-d]pyrimidine-2,7-dione;
5-Amino-3-[(2R,3S,5S)-5-(hydroxymethyl)-3-(1-hydroxypropyl)tetrahydrofuran-2-yl]-6H-thiazolo[4,5-d]pyrimidine-2,7-dione;
5-Amino-3-[(2R,3S,5S)-5-(hydroxymethyl)-3-[hydroxy(phenyl)methyl]tetrahydrofuran-2-yl]-6H-thiazolo[4,5-d]pyrimidine-2,7-dione;
5-Amino-3-[(2R,3S,5S)-3[hydroxy-(2-methoxyphenyl)methyl]-5-(hydroxymethyl)tetrahydrofuran-2-yl]-6H-thiazolo[4,5-d]pyrimidine-2,7-dione;
5-Amino-3-[(2R,3S,5S)-3-[(2-chlorophenyl)-hydroxymethyl]-5-(hydroxymethyl)tetrahydrofuran-2-yl]-6H-thiazolo[4,5-d]pyrimidine-2,7-dione;
5-Amino-3-[(2R3S,5S)-5-(hydroxymethyl)-3-[(S)-hydroxy(2-pyridyl)methyl]tetrahydrofuran-2-yl]-6H-thiazolo[4,5-d]pyrimidine-2,7-dione;
5-Amino-3-[(2R,3S,5S)-5-(hydroxymethyl)-3-(1-hydroxy-1-methyl-ethyl)tetrahydrofuran-2-yl]-6H-thiazolo[4,5-d]pyrimidine-2,7-dione;
[(1R)-1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]ethyl]acetate;
[(1S)-1-[(2R,3S,5S)-2-(5-amino-2,7-dioxo-6H-thiazolo[4,5-d]pyrimidin-3-yl)-5-[(1S)-1-hydroxypropyl]tetrahydrofuran-3-yl]ethyl]acetate;
5-Amino-3-[(2R,3S,5S)-3-[(1R)-1-hydroxyethyl]-5-[(1S)-1-hydroxypropyl]tetrahydrofuran-2-yl]-6H-thiazolo[4,5-d]pyrimidine-2,7-dione;
5-Amino-3-[(2R,3S,5S)-3-[(1S)-1-hydroxyethyl]-5-[(1S)-1-hydroxypropyl]tetrahydrofuran-2-yl]-6H-thiazolo[4,5-d]pyrimidine-2,7-dione;
[(1R)-1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]ethyl]ethyl carbonate;
[(1R)-1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]ethyl]benzoate;
5-Amino-3-[(2R,3S,5S)-5-[(1S)-1-hydroxypropyl]-3-[(1R)-1-methoxyethyl]tetrahydrofuran-2-yl]-6H-thiazolo[4,5-d]pyrimidine-2,7-dione;
5-Amino-3-[(2R,3S,5S)-3-[(1R)-1-benzyloxyethyl]-5-[(1S)-1-hydroxypropyl]tetrahydrofuran-2-yl]-6H-thiazolo[4,5-d]pyrimidine-2,7-dione;
3-[(2R,3S,5S)-3-[(1R)-1-Allyloxyethyl]-5-[(1S)-1-hydroxypropyl]tetrahydrofuran-2-yl]-5-amino-6H-thiazolo[4,5-d]pyrimidine-2,7-dione;
5-Amino-3-[(2R,3S,5S)-5-[(1S)-1-hydroxypropyl]-3-[(1S)-1-methoxyethyl]tetrahydrofuran-2-yl]-6H-thiazolo[4,5-d]pyrimidine-2,7-dione;
[(1S)-1-[(2S,4S,5R)-5-(5-Amino-2,7-dioxo-6H-thiazolo[4,5-d]pyrimidin-3-yl)-4-[(1R)-1-hydroxyethyl]tetrahydrofuran-2-yl]propyl]acetate;
5-Amino-3-[(2R,3S,5S)-3-[hydroxy(phenyl)methyl]-5-[(1S)-1-hydroxypropyl]tetrahydrofuran-2-yl]-6H-thiazolo[4,5-d]pyrimidine-2,7-dione;
[1-[(2R,3S,5S)-2-(5-Amino-2,7-dioxo-6H-thiazolo[4,5-d]pyrimidin-3-yl)-5-[(1S)-1-hydroxypropyl]tetrahydrofuran-3-yl]-1-methyl-ethyl]acetate; and
5-Amino-3-[(2R,3S,5S)-3-(1-hydroxy-1-methyl-ethyl)-5-[(1S)-1-hydroxypropyl]tetrahydrofuran-2-yl]-6H-thiazolo[4,5-d]pyrimidine-2,7-dione;

or a pharmaceutically acceptable salt, enantiomer or diastereomer thereof.

10. A compound according to claim 1 selected from:
5-Amino-3-[(2R,3S,5S)-3-(1-hydroxyethyl)-5-(hydroxymethyl)tetrahydrofuran-2-yl]-6H-thiazolo[4,5-d]pyrimidine-2,7-dione;
5-Amino-3-[(2R,3S,5S)-5-(hydroxymethyl)-3-(1-hydroxy-1-methyl-ethyl)tetrahydrofuran-2 -yl]-6H-thiazolo[4,5-d]pyrimidine-2,7-dione;
5-Amino-3-[(2R,3S,5S)-3-[(1R)-1-hydroxyethyl]-5-[(1S)-1-hydroxypropyl]tetrahydrofuran-2-yl]-6H-thiazolo[4,5-d]pyrimidine-2,7-dione;
[(1S)-1-[(2S,4S,5R)-5-(5-Amino-2,7-dioxo-6H-thiazolo[4,5-d]pyrimidin-3-yl)-4-[(1R)-1-hydroxyethyl]tetrahydrofuran-2-yl]propyl]acetate;
5-Amino-3-[(2R,3S,5S)-3-[hydroxy(phenyl)methyl]-5-[(1S)-1-hydroxypropyl]tetrahydrofuran-2-yl]-6H-thiazolo[4,5-d]pyrimidine-2,7-dione; and
5-Amino-3-[(2R,3S,5S)-3-(1-hydroxy-1-methyl-ethyl)-5-[(1S)-1-hydroxypropyl]tetrahydrofuran-2-yl]-6H-thiazolo[4,5-d]pyrimidine-2,7-dione;
or a pharmaceutically acceptable salt, enantiomer or diastereomer thereof.

11. A process for the preparation of a compound according to claim 1, or a pharmaceutically acceptable salt, enantiomer or diastereomer thereof, comprising:
(a) the reaction of a compound of formula (IVh),

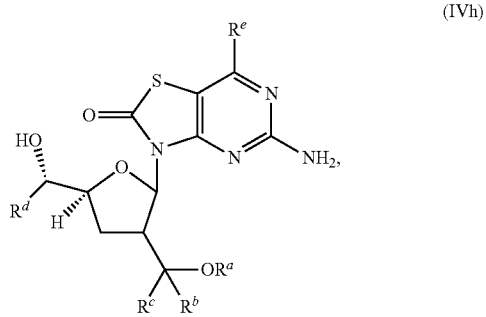

(IVh)

with a base, wherein
$R^a$ is $C_{1-6}$alkylcarbonyl, phenylcarbonyl or trimethylsilyl;
$R^b$ is $R^2$;
$R^c$ is $R^3$;
$R^d$ is $R^4$; and
$R^e$ is OH;
(b) the reaction of a compound of formula (Vd),

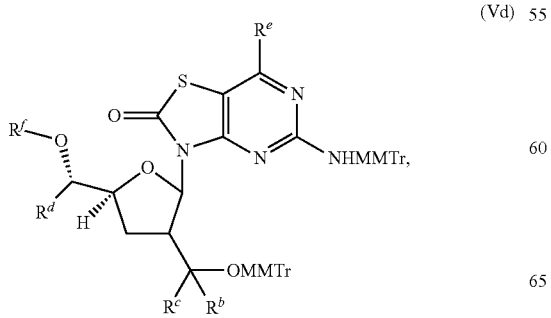

(Vd)

with an acid, wherein
$R^b$ is $R^2$;
$R^c$ is $R^3$;
$R^d$ is $R^4$;
$R^e$ is OH; and
$R^f$ is $R^5$; or
(c) the reaction of a compound of formula (VIe),

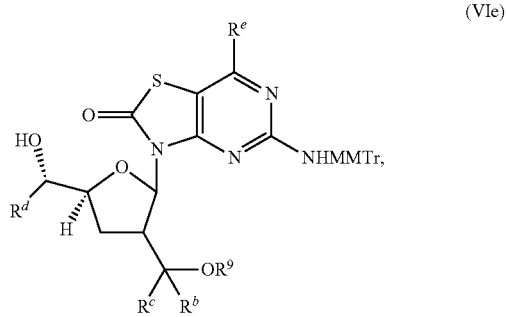

(VIe)

with an acid, wherein
$R^b$ is $R^2$;
$R^c$ is $R^3$;
$R^d$ is $R^4$;
$R^e$ is OH; and
$R^g$ is $R^1$.

12. A pharmaceutical composition comprising a compound according to claim 1, or a pharmaceutically acceptable salt, enantiomer or diastereomer thereof, and a therapeutically inert carrier.

13. A compound according to claim 1, or a pharmaceutically acceptable salt, enantiomer or diastereomer thereof, when manufactured according to a process of claim 11.

14. A method for the treatment or prophylaxis of hepatitis B virus infection, which method comprises administering a therapeutically effective amount of a compound according to claim 1, or a pharmaceutically acceptable salt, enantiomer or diastereomer thereof.

15. A method for agonizing TLR7, which method comprises administering a therapeutically effective amount of a compound according to claim 1, or a pharmaceutically acceptable salt, enantiomer or diastereomer thereof.

16. A method for inducing production of interferon-α, which method comprises administering a therapeutically effective amount of a compound according to claim 1, or a pharmaceutically acceptable salt, enantiomer or diastereomer thereof.

17. A compound of formula (II),

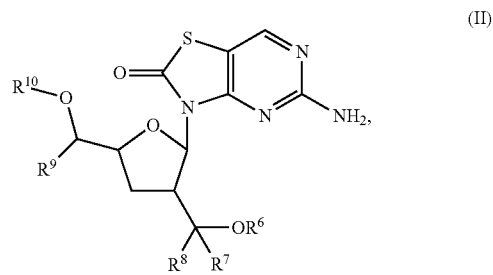

(II)

wherein
$R^6$ is H, $C_{1-6}$alkyl, $C_{2-6}$alkenyl, phenyl$C_{1-6}$alkyl, $C_{1-6}$alkylcarbonyl, $C_{1-6}$alkoxycarbonyl or phenylcarbonyl;
$R^7$ and $R^8$ are independently selected from H, $C_{1-6}$alkyl, $C_{3-7}$cycloalkyl, phenyl and pyridinyl, said phenyl and pyridinyl being unsubstituted or substituted with one to three substituents independently selected from $C_{1-6}$alkyl, halogen and $C_{1-6}$alkoxy;
$R^9$ is H or $C_{1-6}$alkyl; and
$R^{10}$ is H or $C_{1-6}$alkylcarbonyl;
or a pharmaceutically acceptable salt, enantiomer or diastereomer thereof.

18. A compound of formula (IIa) according to claim 17,

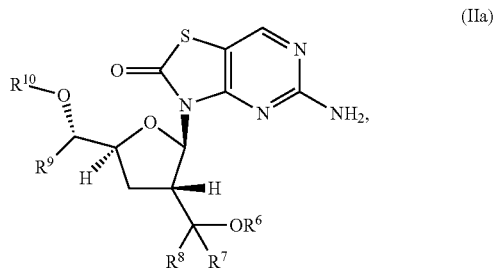

(IIa)

wherein
$R^6$ is H, $C_{1-6}$alkyl, $C_{2-6}$alkenyl, phenyl$C_{1-6}$alkyl, $C_{1-6}$alkylcarbonyl, $C_{1-6}$alkoxycarbonyl or phenylcarbonyl;
$R^7$ and $R^8$ are independently selected from H, $C_{1-6}$alkyl, $C_{3-7}$cycloalkyl, phenyl and pyridinyl, said phenyl and pyridinyl being unsubstituted or substituted with one to three substituents independently selected from $C_{1-6}$alkyl, halogen and $C_{1-6}$alkoxy;
$R^9$ is H or $C_{1-6}$alkyl; and
$R^{10}$ is H or $C_{1-6}$alkylcarbonyl;
or a pharmaceutically acceptable salt, enantiomer or diastereomer thereof.

19. A compound according to claim 17, wherein $R^6$ is H, $C_{1-6}$alkyl, $C_{1-6}$alkylcarbonyl, $C_{1-6}$alkoxycarbonyl or phenylcarbonyl; or a pharmaceutically acceptable salt, enantiomer or diastereomer thereof.

20. A compound according to claim 17, wherein $R^6$ is H, methyl, acetyl, isopropylcarbonyl, tert-butylcarbonyl, isobutylcarbonyl, ethoxycarbonyl or phenylcarbonyl; or a pharmaceutically acceptable salt, enantiomer or diastereomer thereof.

21. A compound according to claim 17, wherein $R^7$ and $R^8$ are independently selected from H, $C_{1-6}$alkyl and phenyl, said phenyl being unsubstituted or substituted with one to three substituents independently selected from $C_{1-6}$alkyl, halogen and $C_{1-6}$alkoxy; provided that $R^7$ and $R^8$ are not H simultaneously; or a pharmaceutically acceptable salt, enantiomer or diastereomer thereof.

22. A compound according to claim 17, wherein $R^7$ and $R^8$ are independently selected from H, methyl, ethyl, phenyl, chlorophenyl and methoxyphenyl; provided that $R^7$ and $R^8$ are not H simultaneously; or a pharmaceutically acceptable salt, enantiomer or diastereomer thereof.

23. A compound according to claim 17, wherein
$R^6$ is H, $C_{1-6}$alkylcarbonyl or $C_{1-6}$alkoxylcarbonyl;
$R^7$ and $R^8$ are independently selected from H and $C_{1-6}$alkyl; provided that $R^2$ and $R^3$ are not H simultaneously;
$R^9$ is $C_{1-6}$alkyl; and
$R^{10}$ is H or $C_{1-6}$alkylcarbonyl;
or a pharmaceutically acceptable salt, enantiomer or diastereomer thereof.

24. A compound according to claim 17, wherein
$R^6$ is H, acetyl, isopropylcarbonyl, tert-butylcarbonyl, isobutylcarbonyl or ethoxycarbonyl;
$R^7$ and $R^8$ are independently selected from H and methyl; provided that $R^7$ and $R^8$ are not H simultaneously;
$R^9$ is ethyl; and
$R^{10}$ is H or acetyl;
or a pharmaceutically acceptable salt, enantiomer or diastereomer thereof.

25. A compound according to claim 17 is selected from:
[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl]acetate;
[(1S)-1-[(2S,4S,5R)-5-(5-Amino-2-oxo-thiazolo[4,5-a]pyrimidin-3-yl)-4-[(1R)-1-hydroxyethyl]tetrahydrofuran-2-yl]propyl]acetate;
[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl]2-methylpropanoate;
[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl]2,2-dimethylpropanoate;
[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl]3-methylbutanoate; and
[(1R)-1-[(2R,3S,5S)-2-(5-Amino-2-oxo-thiazolo[4,5-d]pyrimidin-3-yl)-5-[(1S)-1-hydroxypropyl]tetrahydrofuran-3-yl]ethyl]ethyl carbonate;
or a pharmaceutically acceptable salt, enantiomer or diastereomer thereof.

26. A process for the preparation of a compound according to claim 17, or a pharmaceutically acceptable salt, enantiomer or diastereomer thereof, comprising:
(a) the reaction of a compound of formula (IVh),

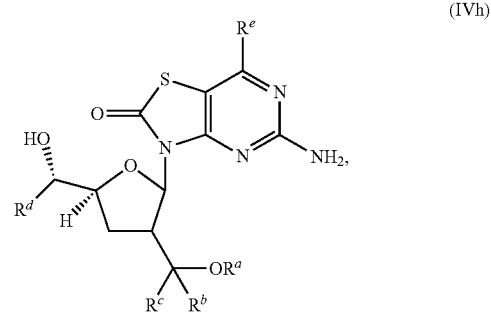

(IVh)

with a base, wherein
$R^a$ is $C_{1-6}$alkylcarbonyl, phenylcarbonyl or trimethylsilyl;
$R^b$ is $R^7$;
$R^c$ is $R^8$;
$R^d$ is $R^9$; and
$R^e$ is H;

(b) the reaction of a compound of formula (Vd),

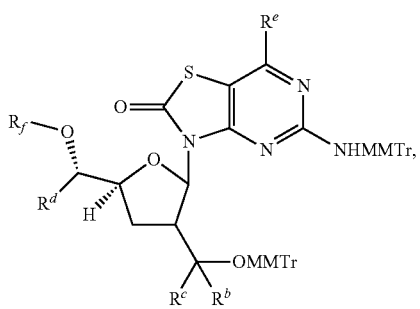
(Vd)

with an acid, wherein
$R^b$ is $R^7$;
$R^c$ is $R^8$;
$R^d$ is $R^9$;
$R^e$ is H; and
$R^f$ is $R^{10}$; or (c) the reaction of a compound of formula (VIe),

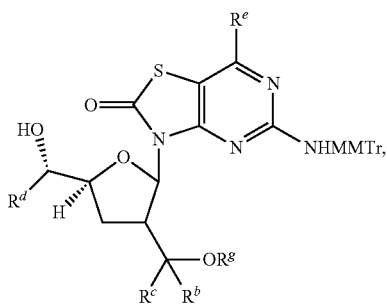
(VIe)

with an acid, wherein
$R^b$ is $R^7$;
$R^c$ is $R^8$;
$R^d$ is $R^9$;
$R^e$ is H; and
$R^g$ is $R^6$.

27. A pharmaceutical composition comprising a compound according to claim 17, or a pharmaceutically acceptable salt, enantiomer or diastereomer thereof, and a therapeutically inert carrier.

28. A compound according to claim 17, or a pharmaceutically acceptable salt, enantiomer or diastereomer thereof, when manufactured according to a process of claim 26.

29. A method for the treatment or prophylaxis of hepatitis B virus infection, which method comprises administering a therapeutically effective amount of a compound according to claim 17, or a pharmaceutically acceptable salt, enantiomer or diastereomer thereof.

30. A method for agonizing TLR7, which method comprises administering a therapeutically effective amount of a compound according to claim 17, or a pharmaceutically acceptable salt, enantiomer or diastereomer thereof.

31. A method for inducing production of interferon-α, which method comprises administering a therapeutically effective amount of a compound according to claim 17, or a pharmaceutically acceptable salt, enantiomer or diastereomer thereof.

* * * * *